US 9,630,964 B2

(12) United States Patent
Rommelspacher et al.

(10) Patent No.: US 9,630,964 B2
(45) Date of Patent: Apr. 25, 2017

(54) FLUORO-9-METHYL-β-CARBOLINES

(71) Applicant: AudioCure Pharma GmbH, Berlin (DE)

(72) Inventors: Hans Rommelspacher, Berlin (DE); Christoph Enzensperger, Jena (DE)

(73) Assignee: Audiocure Pharma GMBH, Berlin (DE)

( * ) Notice: Subject to any disclaimer, the term of this patent is extended or adjusted under 35 U.S.C. 154(b) by 0 days.

(21) Appl. No.: 15/025,538

(22) PCT Filed: Sep. 29, 2014

(86) PCT No.: PCT/EP2014/070840
§ 371 (c)(1),
(2) Date: Mar. 28, 2016

(87) PCT Pub. No.: WO2015/044434
PCT Pub. Date: Apr. 2, 2015

(65) Prior Publication Data
US 2016/0214981 A1    Jul. 28, 2016

(30) Foreign Application Priority Data
Sep. 29, 2013 (EP) .................... 13186560

(51) Int. Cl.
C07D 471/04    (2006.01)
(52) U.S. Cl.
CPC ................. C07D 471/04 (2013.01)
(58) Field of Classification Search
CPC ...................................... C07D 8/31
See application file for complete search history.

(56) References Cited

U.S. PATENT DOCUMENTS 8,334,299 B2    12/2012  Rommelspacher
9,107,914 B2     8/2015  Rommelspacher
2004/0038970 A1  2/2004  Thurieau et al.

FOREIGN PATENT DOCUMENTS

DE    WO 2011079841 A1 *  7/2011  ........... A61K 9/0046

OTHER PUBLICATIONS

Castro et al., "Novel IKK Inhibitors: Beta-Carbolines," Bioorganic & Medical Chemistry Letters, Pergamon, vol. 13, No. 14, 2003, pp. 2419-2422.
Hamann et al., "9-Methyl-β-Carboline Up-Regulates the Appearance of Differentiated Dopaminergic Neurones in Primary Mesencephalic Culture," Neurochemistry International 2008, 52, pp. 688-700.
Rommelspacher et al., "The Levels of Norharman are High Enough After Smoking to Affect Monoamineoxidase B in Platelets," European Journal of Pharmacology, vol. 441 (1-2), 2002, pp. 115-125.
Valkó K, "Application of High-Performance Liquid Chromatography Based Measurements of Lipophilicity to Model Biological Distribution," Journal of Chromatography A 2004; 1037 (1-2): 299-310.

* cited by examiner

Primary Examiner — Benjamin Packard
(74) Attorney, Agent, or Firm — Knobbe, Martens, Olson & Bear LLC

(57) ABSTRACT

The present invention relates to fluoro-9-methyl-β-carbolines, their preparation as well as their medical use and pharmaceutical compositions containing fluoro-9-methyl-β-carbolines.

10 Claims, 17 Drawing Sheets

AC-002 (earlier experiment)

FLUORO-9-METHYL-β-CARBOLINES

The present invention relates to fluoro-9-methyl-β-carbolines, their preparation as well as their medical use and pharmaceutical compositions containing Fluoro-9-methyl-β-carbolines.

The compounds according to the invention serve for treatment of acute and chronic ear diseases and hearing damages, dizziness and balance disturbances especially of hearing loss, blast trauma, blast injury, tinnitus, labyrinthine deafness caused by chronic exposure to noise, age-related hearing loss, trauma during implantation of inner-ear prostheses (insertion trauma), dizziness caused by diseases in the inner ear area, dizziness associated with and/or as symptom of Meniere's disease, balance disturbances associated with and/or as symptom of Meniere's disease, and hearing damages due to antibiotics and cytostatic agents.

According to research of the World Health Organization (WHO) approximately 250 million people suffer from mild and severe hearing disorders. In the USA 30 to 40 million people are affected by hearing damages and hearing losses. The costs of treatment alone are approximately 50 billion USD every year. The German association for the hearing impaired (Deutscher Schwerhörigenbund) has reported in 2007 that ca. 19% of the German population from the age of 14 suffer from hearing disorders.

With increasing age the percentage of hearing impaired rises. Even now hearing disorders constitute at people over 65 the fourth most chronic physical impairment, after diseases of bones and joints, high blood pressure and heart diseases. 37% of the people between 60 to 69 years and 54% of the people from 70 years of age are affected by hearing damages. In the Federal Republic of Germany approximately 12-15 million patients suffer from labyrinthine deafness and approximately 2.9 million patients from tinnitus.

The term "Tinnitus aurium" or in short tinnitus means a symptom or also syndrome at which the affected person perceives lasting or recurring noises, wherein two types of tinnitus can be distinguished. At the relatively rare "objective tinnitus" noises perceived by the patient can also be perceived from outside or at least can be measured. They are usually based on a body's own sound source as for instance a blood vessel passing closely the inner ear. At the significantly more frequent "subjective tinnitus" the acoustic phenomena do not rest on an external source perceptible for other persons. So that "subjective tinnitus" is an acoustic perception that independent of a sound acting on the ear, is perceived by the patient. The causes for these perceptions may be diverse and among others attributable to a disorder of the hearing function of the inner ear. The type of apparent noises which the tinnitus patient perceives is very diverse. The term tinnitus combines the following acoustic impressions:

humming or whistle sound
hissing
rushing
snapping or knocking

The noise may be constant in its intensity; it may also have a rhythmically-pulsating character.

The ear is built up as follows. From the earlobes leads the auditory canal into the inside of the ear. The auditory canal ends at the eardrum. This part of the ear is denoted as outer ear. Behind the outer ear lies a space, the middle ear, also called tympanum, which is connected to the eustachian tube and also to the nasopharynx. The middle ear is enclosed by the eardrum on its one side and by the oval window and the round window on the opposite side. Behind both windows follows a space denoted as inner ear. The inner ear houses several organs like the balance system (vestibular apparatus) and the so called snail (cochlea) for acoustic perception. This again comprises the organ of corti as carrier of the sensory cells (hair cells) in the inner ear.

The membrane of the round window forms a biologic barrier to the inner ear space and constitutes the biggest obstacle for local therapy of damages and diseases of the inner ear. The administered active agent must overcome this membrane in order to enter the inner ear space. The active agent cannot be administered mechanically and instrument-based through the membrane, because the membrane would be damaged by this manipulation. It may be operatively (i.e. injection through the ear drum) administered locally at the round window membrane and then may penetrate the round window membrane. Consequently, the active agent reaches the perilymph filled inner ear space that is formed by the interconnected compartments of the cochlea, namely the scala tympani and the scala vestibule. The compartment separated by membranes between the scala tympani and the scala vestibule which is called scala media contains sensory cells of the hearing organ (inner and outer hair cells) surrounded by endolymphs. These are denoted together with the surrounding supporting cells as organ of corti. The hair cells are at labyrinthine deafness of any cause (age, medicaments like certain antibiotics or cytostatic agents) as well as at tinnitus primarily damaged. Over the membranes that separate the scala media from the perilymphatic space, active agents may get to the hair cells directly or through the endolymphs. Because the perilymphatic as well as the endolymphatic compartments of the cochlea are in connection to the balance system, active agents may get from the cochlea also into the sensory cells of the vestibular apparatus.

The German patent application (DE 10 2007 009264 A1) discloses 9-alkyl-β-carbolines that due to their neuroprotective effect can be used for therapy and/or prophylaxis of movement disorders and/or neurologic diseases like for instance Alzheimer or Parkinson.

Von Hamann et al. (J. Hamann et al.; *Neurochem Internat.* 2008, 52, 688-700) were able to show a neuroprotective effect of the β-carboline 9-methyl-β-carboline at primary cell cultures of mesencephalic neurons. The increased survival rate of neurons due to 9-methyl-β-carboline shown there was however not caused by an increased proliferation. On the contrary, the application of 9-methyl-β-carboline led to an inhibition of the proliferation and to an increased differentiation of neurons. This effect of 9-methyl-β-carboline was confirmed on human neuroblastoma cells (SH-SY5Y). Along with the promoted differentiation, an increased expression of neurotrophic factors like sonic hedgehog, Wnt1 and Wnt5a was proven. Moreover, a 9-methyl-β-carboline induced raise of the number of dopaminergic neurons appeared in the primary cell culture of mesencephalic neurons. Thus, a therapeutic benefit of 9-methyl-β-carboline in the treatment of Parkinson is hold out in prospect.

The US patent application (US 2004/038970 A1) discloses the use of β-carbolines as active agents in the treatment of a variety of medical indications, including tinnitus, whereas however from 9-alkyl-β-carbolines and therefore also from 6- and/or 7-fluoro-9-methyl-carbolines structurally highly deviating group of β-carbolines is mentioned.

The international patent application (WO 2011/079841) discloses β-carbolines especially 9-alkyl-β-carbolines and their use for treatment of diseases or damages of the inner ear. It was shown, that the application of 9-alkyl-β-carbolines promotes the neuronal differentiation of human neuroblastoma cells (SH-SY5Y) as well as the expression of neurotrophic factors with neuroprotective properties. This was confirmed in cell cultures of cochlea preparations of a rat. Additionally, it was shown at a guinea pig, that 9-methyl-β-carboline after local application at the round window of the inner ear can diffuse in the perilymphatic space of the inner ear and it leads to an increase of the electrophysiologic activity of the hair sensory cells of the organ of corti.

The primary object of the present invention is to provide an active agent as well as pharmaceutical compositions which may be used for prophylaxis and treatment of hearing damages, age-related hearing loss (presbyacusis), dizziness and balance disturbances as well as for improving learning and memory and which may show an advantage over the state of the art.

The objective of the present invention is solved by the teaching of the independent claims. Further advantageous features, aspects and details of the invention are evident from the dependent claims, the description, the figures, and the examples of the present application.

Fluoro-9-methyl-β-carbolines

Surprisingly, it has been found, that according to the invention Fluoro-9-methyl-β-carbolines of general formula (I) show increased efficacy in treatment of inner ear diseases in comparison to compounds from the prior art (e.g. 9-methyl-β-carboline). They offer the possibility to be applied in lower doses and reduced toxicity which represents a significant therapeutic improvement in comparison to the prior art.

In addition, it has been surprisingly found, that according to the invention 6- and/or 7-fluoro-9-methyl-β-carbolines by special properties stand out from the state of the art that support a therapeutic use. Thus for the 6- and/or 7-fluoro-9-methyl-β-carbolines in comparison to 9-methyl-β-carboline an increased efficacy on promoting neuronal differentiation in human neuroblastoma cells was proven. Furthermore, 6- and/or 7-fluoro-9-methyl-β-carbolines in comparison to 9-methyl-β-carboline show a significantly increased lipophilicity which is associated with increased membrane permeability. This has far-reaching consequences for therapeutic use of the compound according to the invention for treatment of diseases or damages of the inner ear or for improving memory and increasing learning ability. As already described, biologic membranes like the eardrum, the membrane of the round window and the membranes of scala media (membrane tectoriana and Reissner's membrane), form a natural obstacle for an active agent on its way to the hair cells of the inner ear. This applies in particular to the topical application of an active agent on the ear drum or the round window. Due to the increased membrane permeability the availability of the active agent is also increased. Besides the membrane permeability the degradation of an active agent in the body plays an important role for its efficacy, especially when administered systemically and also for possible side effects. While 9-methyl-β-carboline is degraded by hydroxylation at position 6 with subsequent conjugation reaction, for 6-fluoro-9-methyl-β-carboline this metabolic pathway is blocked by fluoride group(s). Hereby, not only the half time of 6-fluoro-9-methyl-β-carboline was increased, also the risk for forming potentially toxic degradation products was reduced. Due to the increased efficacy of 6- and/or 7-fluoro-9-methyl-β-carboline a lowered dose in therapy in comparison to other 9-alkyl-β-carbolines seems to be possible. This is especially of great importance for long-term therapy of chronic diseases, because the burden of the body and moreover undesirable side effects can be reduced. Consequently, the present application is a selection invention.

The term "6- and/or 7-fluoro-9-methyl-β-carboline" refers to either compound 6-fluoro-9-methyl-β-carboline or compound 7-fluoro-9-methyl-β-carboline, when linked with "or" and to compounds 6-fluoro-9-methyl-β-carboline and 7-fluoro-9-methyl-β-carboline, when linked with "and".

The present invention relates to compounds of general formula (I) or fluoro-9-methyl-β-carbolines of general formula (I):

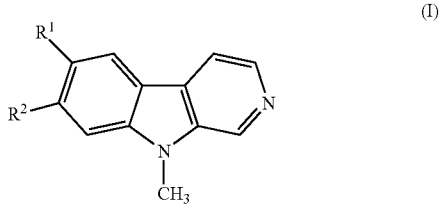

(I)

wherein $R^1$ is —F and $R^2$ is —H or —F, or
wherein $R^1$ is —H and $R^2$ is —F;
as well as pharmacologically acceptable salts, solvates and hydrates as well as prodrugs and complex compounds of the aforementioned compounds.

The present invention relates also to compounds of general formula (I) or fluoro-9-methyl-β-carbolines of general formula (I):

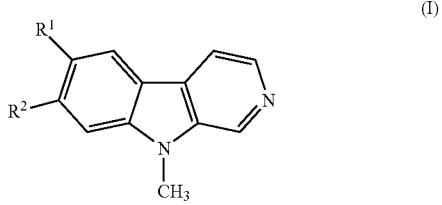

(I)

wherein $R^1$ and $R^2$ are independently of each other —F or —H, and
wherein at least one of both residues $R^1$ or $R^2$ is —F;
as well as pharmacologically acceptable salts, solvates and hydrates as well as pro drugs and complex compounds of the aforementioned compounds.

The present invention relates also to compounds of general formula (I) or fluoro-9-methyl-β-carbolines of general formula (I):

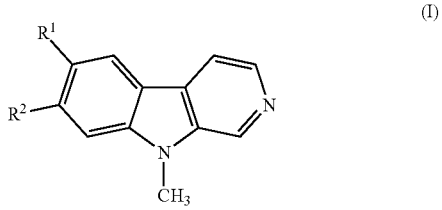

(I)

wherein $R^1$ and $R^2$ are independently of each other —F or —H, and wherein at least one of both residues R¹ or R² is —H;
as well as pharmacologically acceptable salts, solvates and hydrates as well as pro drugs and complex compounds of the aforementioned compounds.

It is preferred when R¹ is —F and R² is —H or when R¹ is —H and R² is —F.

The herein used term prodrug is defined as a pharmacological substance that is administered in an inactive or less effective form. After administration, it is converted into its active, effective form, i.e. a fluoro-9-methyl-β-carboline of general formula (I), in the patient's body.

Possible acids, which can form an acid addition salt with the compound of present invention, may be the following: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxypropanedioic acid), fumaric acid, citric acid, ascorbic acid, maleic acid, malonic acid, hydroxymaleic acid, pyruvic acid, phenylacetic acid, (o-, m-, p-) toluoylic acid, benzoic acid, p-aminobenzoic acid, p-hydroxybenzoic acid, salicylic acid, p-aminosalicylic acid, methansulfonic acid, ethansulfonic acid, hydroxyethansulfonic acid, ethylenesulfonic acid, p-toluenesulfonic acid, naphthalenesulfonic acid, naphthylaminesulfonic acid, sulphanilic acid, camphersulfonic acid, china acid (quinic acid), o-methyl-mandelic acid, hydrogenbenzenesulfonic acid, picric acid (2,4,6-trinitrophenol), adipinic acid, d-o-tolyltartaric acid, amino acids like methionine, tryptophane, arginine, and especially acidic amino acids like glutamic acid or aspartic acid. Furthermore betaine-types are also possible A further aspect of the present invention relates a process for preparation of compounds according to the invention of general formula (I) (and a fluoro-9-methyl-β-carboline of general formula (I), respectively), comprising following steps:
 a) reaction of starting material of general formula (II) (and a fluoro-1-methyltryptamine hydrochloride of general formula (II), respectively) under addition of glyoxylic acid hydrate of formula (III) and a base to a compound of general formula (IV)

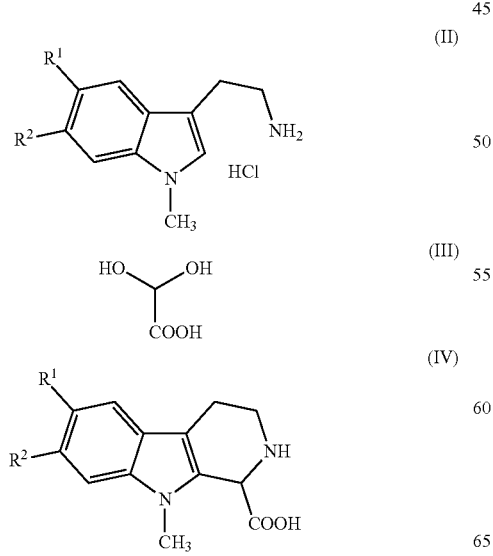

b) decarboxylation of compound of general formula (IV) under addition of an acid and under heating to a compound of general formula (V) (and to a fluoro-9-methyl-2,3,4,9-tetrahydro-β-carboline of general formula (V), respectively)

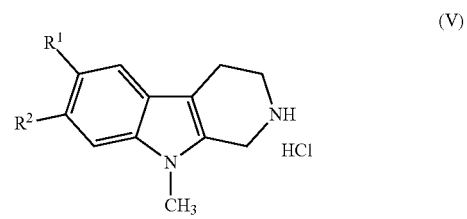

c) aromatization of compound of general formula (V) (and of fluoro-9-methyl-2,3,4,9-tetrahydro-β-carboline of general formula (V), respectively) to a compound of general formula (I) (and to fluoro-9-methyl-β-carboline of general formula (I), respectively) under addition of a catalyst;
wherein
R¹ is —F and R² is —H or —F, or
R¹ is —H and R² is —F.

There is no need to say that the representation of residues R¹ and R², as described above, for a certain process for preparation of a compound according to the invention applies not only for the starting material of the corresponding synthesis, but also for the obtained intermediate products as well as final end product of the synthesis.

A further aspect of the present invention relates therefore to a process for preparation of a compound according to the invention of general formula (I) (and a fluoro-9-methyl-β-carboline of general formula (I), respectively) comprising following steps:
 a) reaction of starting material of general formula (II) (and a fluoro-1-methyltryptamine hydrochloride of general formula (II), respectively) under addition of glyoxylic acid hydrate of formula (III) and a base to a compound of general formula (IV)

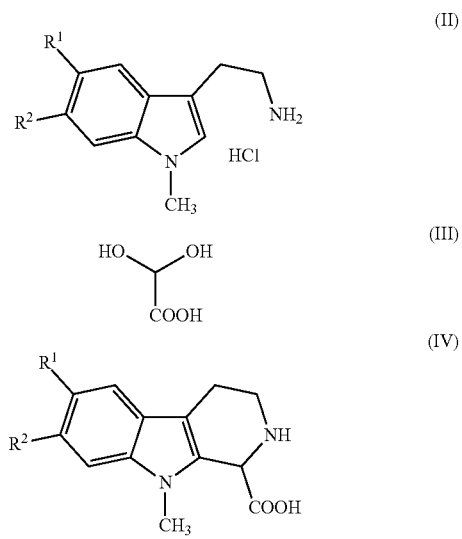

b) decarboxylation of compound of general formula (IV) under addition of an acid and under heating to a compound of general formula (V) (and to a fluoro-9-methyl-2,3,4,9-tetrahydro-β-carboline of general formula (V), respectively)

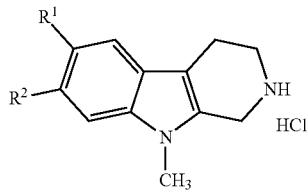

c) aromatization of compound of general formula (V) (and of fluoro-9-methyl-2,3,4,9-tetrahydro-β-carboline of general formula (V), respectively) to a compound of general formular (I) (and to fluoro-9-methyl-β-carboline of general formula (I), respectively) under addition of a catalyst;

wherein $R^1$ is —F and $R^2$ is —H or —F and this holds equally true for compounds of general formula (I), (II), (IV) and (V), or wherein $R^1$ is —H and $R^2$ is —F and this holds equally true for compounds of general formula (I), (II), (IV) and (V).

Fluoro-1-methyltryptamine hydrochlorides as starting materials are commercially available (see also below). In a preferred embodiment of the invention in step a) a pH-value between 2 and 6, preferably between 3 and 5 and especially preferably a pH-value of 4 is achieved by addition of base. In a further preferred embodiment in step a)' the crystallization of compound IV is promoted by incubating in ice water.

In a further preferred embodiment the reaction in step b) takes place under inert gas, especially preferred under $N_2$. Furthermore, it is preferred to promote the crystallization of reaction product of step b) by a step b)' incubation at cold, especially preferred between 0° C. and 5° C. for several hours. In a further preferred embodiment for purification of reaction product of step b), a recrystallization from methanol is conducted after crystallization. Furthermore, it is preferred that fluoro-9-methyl-2,3,4,9-tetrahydro-β-carbolines (and compounds of general formula (V), respectively), in step c) are dissolved in water first and by addition of base, e.g. sodium hydroxide or sodium carbonate, to adjust an alkaline pH-value, especially preferred a pH-value between pH 11 and pH 14, especially preferred pH 13.

In a preferred embodiment the catalyst for oxidative aromatization in step c) may be among others Pd/C, Pt/C, $PdCl_2$, Pd/sepiolite, $Pd/SiO_2$ and $Pd/AlO_4$. Further additives which enable oxidative aromatization are known to the person skilled in the art. However, Pd/C (palladium on carbon, palladium on activated carbon) is preferably used as catalyst.

The bases added in step a) and c) can be independently of each other inorganic or organic bases, e.g. NaOH, KOH, $NH_4OH$, tetraalkylammonium hydroxide, lysine or arginine. The person skilled in the art knows which bases are suitable here for running the reaction. Preferred are however KOH and NaOH, respectively.

The acid added in step b) may be an inorganic or organic acid, e.g. hydrochloric acid, hydrobromic acid, sulfuric acid, phosphoric acid, acetic acid, citric acid, oxalic acid, malic acid, salicylic acid, p-aminosalicylic acid, malonic acid, fumaric acid, succinic acid, ascorbic acid, maleinic acid, sulfonic acid, phosphonic acid, perchloric acid, nitric acid, formic acid, propionic acid, gluconic acid, lactic acid, tartaric acid, hydroxymaleinic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylensulfonic acid, p-toluenesulfonic acid, naphthylsulfonic acid, sulfanilic acid, camphersulfonic acid, china acid, mandelic acid, o-methylmandelic acid, hydrogenebenzenesulfonic acid, picric acid, adipic acid, d-o-tolyltartaric acid, tartronic acid, α-toluic acid, (o-, m-, p-) toluic acid, or naphthylaminesulfonic acid. The person skilled to the art knows which acid is suitable here for running the reaction. However, hydrochloric acid is preferred.

According to further embodiments, the present invention is addressed to fluoro-9-methyl-β-carboline of general formula (I)

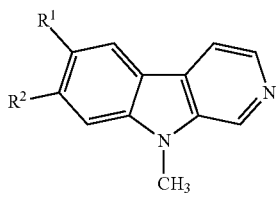

wherein $R^1$ is —F and $R^2$ is —F, even more preferred wherein $R^1$ is —H and $R^2$ is —F, and most preferred wherein $R^1$ is —F and $R^2$ is —H.

6-Fluoro-9-methyl-β-carboline (6F9MβC)

According to an especially preferred embodiment, the present invention relates to the β-carboline 6-fluoro-9-methyl-β-carboline whose preparation as well as whose medical use and pharmaceutical compositions containing 6-fluoro-9-methyl-β-carboline.

The compound 6-fluoro-9-methyl-β-carboline will be herein partly also abbreviated to "6F9MβC" or "AC102". The 9-methyl-β-carboline known in the prior art will be on the other hand partly abbreviated to "9MβC" or "AC002".

The compound according to the invention 6-fluoro-9-methyl-β-carboline is not disclosed in the prior art more individualized i.e. in a concrete form. In addition, it was surprisingly found, that the inventive 6-fluoro-9-methyl-β-carboline clearly differs from prior art by its special properties which support a therapeutic use. Thus, for the inventive 6-fluoro-9-methyl-β-carboline in comparison to 9-methyl-β-carboline an increased efficacy on promoting neuronal differentiation in human neuroblastoma cells was proven (see example 2). Furthermore, 6-fluoro-9-methyl-β-carboline shows in comparison to 9-methyl-β-carboline a significantly increase lipophilicity, which is associated with an increased membrane permeability. This has far-reaching consequences for the therapeutic use of the compound according to the invention for treatment of diseases and damages of the inner ear, respectively. As already described, biologic membranes like the eardrum, the membrane of the round window and the membranes of scala media (membrane tectoriana and Reissner's membrane), form a natural obstacle for an active agent on its way to the hair cells of the inner ear. This applies in particular to the topical application of an active agent on the ear drum or the round window. Due to the increased membrane permeability the availability of the active agent is also increased. Besides the membrane permeability the degradation of an active agent in the body plays an important role for its efficacy, especially when administered systemically and also for possible side effects. While 9-methyl-β-carboline is degraded by hydroxylation at position 6 with subsequent conjugation reaction, for 6-fluoro-9-methyl-β-carboline this metabolic pathway is blocked by the fluoride group. Hereby, not only the half time of 6-fluoro-9-methyl-β-carboline was increased, also the risk for forming potentially toxic degradation products was reduced. Due to the increased efficacy of 6- and/or 7-fluoro-9-methyl-β-carboline a lowered dose in therapy in comparison to other 9-alkyl-β-carbolines seems to be possible. This is especially of great importance for long-term therapy of chronic diseases, because the burden of the body and moreover undesirable side effects can be reduced.

The present invention relates to the compound 6-fluoro-9-methyl-β-carboline of formula (Ia)

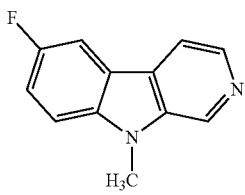

(Ia)

as well as pharmacological acceptable salts, solvates and hydrates as well as prodrugs and complex compounds of the aforementioned compounds.

The herein used term prodrug is defined as a pharmacologic substance that is administered in an inactive or less effective form. After administration, it is converted into its active, effective form, in the above case the 6-fluoro-9-methyl-β-carboline.

Possible acids, which can form an acid addition salt with the inventive 6-fluoro-9-methyl-β-carboline, may be the following: sulfuric acid, sulfonic acid, phosphoric acid, nitric acid, nitrous acid, perchloric acid, hydrobromic acid, hydrochloric acid, formic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxypropanedioic acide), fumaric acid, citric acid, ascorbic acid, maleic acid, malonic acid, hydroxymaleic acid, pyruvic acid, phenylacetic acid, (o-, m-, p-) toluoylic acid, benzoic acid, p-aminobenzoic acid, p-hydroxybenzoic acid, salicylic acid, p-aminosalicylic acid, methansulfonic acid, ethansulfonic acid, hydroxyethansulfonic acid, ethylenesulfonic acid, p-toluenesulfonic acid, naphthalenesulfonic acid, naphthylaminesulfonic acid, sulphanilic acid, camphersulfonic acid, china acid (quinic acid), o-methyl-mandelic acid, hydrogenbenzenesulfonic acid, picric acid (2,4,6-trinitrophenol), adipinic acid, d-o-tolyltartaric acid, amino acids like methionine, tryptophane, arginine, and especially acidic amino acids like glutamic acid or aspartic acid. Furthermore, betaine-types are also possible A further aspect of the present invention relates to a process for preparation of the inventive compound 6-fluoro-9-methyl-β-carboline, comprising the following steps:

a) Reaction of starting material 5-fluoro-1-methyl-tryptamine hydrochloride of formula (IIa) under addition of glyoxylic acid hydrate of formula (III) and a base to a compound of formula (IVa)

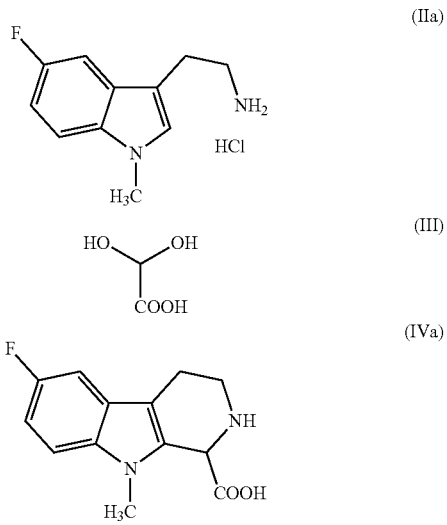

b) Decarboxylation of compound of formula (IVa) under addition of an acid and under heating to 6-fluoro-9-methyl-2,3,4,9-tetrahydro-β-carboline of formula (Va)

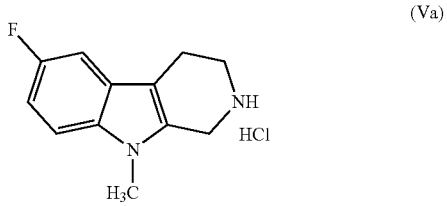

c) Aromatization of 6-fluoro-9-methyl-2,3,4,9-tetrahydro-β-carboline (Va) to 6-fluoro-9-methyl-β-carboline (Ia) under addition of a catalyst.

The starting material 5-fluoro-1-methyltryptamine hydrochloride is commercially available, for instance from AKos GmbH (Steinen). In a preferred embodiment of the invention in step a) a pH-value between 2 and 6, preferably between 3 and 5 and especially preferably a pH-value of 4 is achieved by addition of base. In a further preferred embodiment in step a)' the crystallization of compound IVa is promoted by incubating in ice water.

In a further preferred embodiment the reaction in step b) takes place under inert gas, especially preferred under $N_2$. Furthermore, it is preferred to promote the crystallization of reaction product of step b) by a step b)' incubation at cold, especially preferred between 0° C. and 5° C. for several hours. In a further preferred embodiment for purification of reaction product of step b), a recrystallization from methanol is conducted after crystallization. Furthermore, it is preferred that 6-fluoro-9-methyl-2,3,4,9-tetrahydro-β-carboline in step c) is dissolved in water first and by addition of base, e.g. sodium hydroxide or sodium carbonate, to adjust an alkaline pH-value, especially preferred a pH-value between pH 11 and pH 14, especially preferred pH 13.

In a preferred embodiment the catalyst for oxidative aromatization in step c) may be among others Pd/C, Pt/C, $PdCl_2$, Pd/sepiolite, $Pd/SiO_2$ and $Pd/AlO_4$. Further additives which enable oxidative aromatization are known to the person skilled in the art. However, Pd/C (palladium on carbon, palladium on activated carbon) is preferably used as catalyst.

The bases added in step a) and c) can be independently of each other inorganic or organic bases, e.g. NaOH, KOH, NH₄OH, tetraalkylammonium hydroxide, lysine or arginine. The person skilled in the art knows which bases are suitable here for running the reaction. Preferred are however KOH and NaOH, respectively.

The acid added in step b) may be an inorganic or organic acid, e.g. hydrochloric acid, hydrobromic acid, sulfuric acid, phosphoric acid, acetic acid, citric acid, oxalic acid, malic acid, salicylic acid, p-aminosalicylic acid, malonic acid, fumaric acid, succinic acid, ascorbic acid, maleinic acid, sulfonic acid, phosphonic acid, perchloric acid, nitric acid, formic acid, propionic acid, gluconic acid, lactic acid, tartaric acid, hydroxymaleinic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylensulfonic acid, p-toluenesulfonic acid, naphthylsulfonic acid, sulfanilic acid, camphersulfonic acid, china acid, mandelic acid, o-methylmandelic acid, hydrogenebenzenesulfonic acid, picric acid, adipic acid, d-o-tolyltartaric acid, tartronic acid, α-toluic acid, (o-, m-, p-) toluic acid, or naphthylaminesulfonic acid. The person skilled to the art knows which acid is suitable here for running the reaction. However, hydrochloric acid is preferred.

It was surprisingly found, that the inventive compound 6-fluoro-9-methyl-β-carboline (Ia) in comparison to already known and tested β-carbolines like 9-methyl-β-carboline shows an increased efficacy on treating of inner ear diseases. This was shown on both examination on active agent induced gene expression of important cellular factors (see example 4), which are of significance for cellular regeneration (particularly in the inner ear) after traumas, and in histologic (see example 6) as well as physiologic examinations (see example 7) on regeneration of the auditory system after an acoustic trauma. Additionally, several experiments show a significantly increased lipophilicity (see example 3) of the inventive compound compound 6-fluoro-9-methyl-β-carboline (Ia). Towards the reference substance 9-methyl-β-carboline the following advantages arise among others:
1. Membrane permeability is increased.
2. Elimination is slowed down (elimination half time of 6F9MβC is approximately 1.75-times higher than of 9MβC).
3. Because it is known from other β-carbolines, that they are degraded by hydroxylation at position 6 and subsequent conjugation reaction, blocking this metabolic pathway by the fluoride group at position 6 results in:
   improved bioavailability after oral application.
   minimized risk of toxic metabolites or potentially allergenic metabolites.
4. Yet another known metabolic pathway of β-carbolines, which leads to toxic di-methylated degradation products, proceeds over a sequential N-methylation in vivo, wherein at first the nitrogen at position 2 and then the nitrogen at position 9 is methylated. In current experiments it was shown, that 6F9MβC fortunately does not lead to toxic di-methylated products (see example 8), whereby the risk of toxic metabolites is further minimized.
5. Increased efficacy on active agent induced gene expression of important cellular factors (example 4), which are of significance for cellular regeneration (particularly in the inner ear) after traumas, and also in histologic (see example 6) as well as physiologic examinations (see example 7) on regeneration of the auditory system after an acoustic trauma.

7-Fluoro-9-methyl-β-carboline (7F9MβC)

According to a further embodiment, the present invention relates to the β-carboline 7-fluoro-9-methyl-β-carboline whose preparation as well as whose medical use and pharmaceutical compositions containing 7-fluoro-9-methyl-β-carboline.

The compound 7-fluoro-9-methyl-β-carboline will be herein also partly abbreviated to "7F9MβC".

The present invention relates to compound 7-fluoro-9-methyl-β-carboline of formula (Ib)

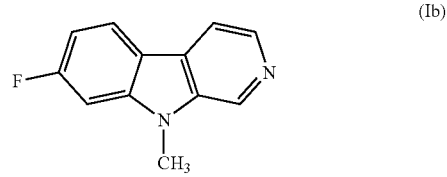

(Ib)

as well as pharmacological acceptable salts, solvates and hydrates as well as prodrugs and complex compounds of the aforementioned compounds.

As explained above, the herein used term prodrug is defined as a pharmacologic substance that is administered in an inactive or less effective form. After administration, it is converted into its active, effective form, in the above case the 7-fluoro-9-methyl-β-carboline.

Possible acids, which can form an acid addition salt with the inventive 7-fluoro-9-methyl-β-carboline, may be the following: sulfuric acid, sulfonic acid, phosphoric acid, nitrous acid, perchloric acid, hydrobromic acid, hydrochloric acid, formic acid, acetic acid, propionic acid, succinic acid, oxalic acid, gluconic acid (glyconic acid, dextronic acid), lactic acid, malic acid, tartaric acid, tartronic acid (hydroxymalonic acid, hydroxypropanedioic acid), fumaric acid, citric acid, ascorbic acid, maleic acid, hydroxymaleic acid, pyruvic acid, phenylacetic acid, (o-, m-, p-) toluoylic acid, benzoic acid, p-aminobenzoic acid, p-hydroxybenzoic acid, salicylic acid, p-aminosalicylic acid, methansulfonic acid, ethansulfonic acid, hydroxyethansulfonic acid, ethylenesulfonic acid, p-toluenesulfonic acid, naphthalenesulfonic acid, naphthylaminesulfonic acid, sulphanilic acid, camphersulfonic acid, china acid (quinic acid), o-methylmandelic acid, hydrogenbenzenesulfonic acid, picric acid (2,4,6-trinitrophenol), adipinic acid, d-o-tolyltartaric acid, amino acids like methionine, tryptophane, arginine, and especially acidic amino acids like glutamic acid or aspartic acid. Furthermore betaine-types are also possible A further aspect of the present invention relates to a process for preparation of the inventive compound 7-fluoro-9-methyl-β-carboline, comprising the following steps:
  a) Reaction of starting material 6-fluoro-1-methyl-tryptamine hydrochloride of formula (IIb) under addition of glyoxylic acid hydrate of formula (III) and a base to a compound of formula (IVb)

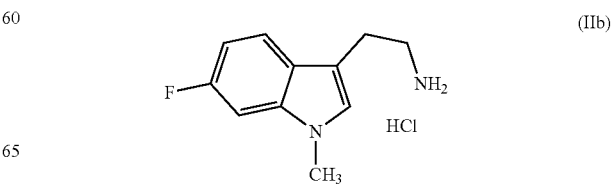

(IIb)

-continued

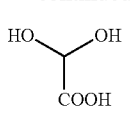
(III)

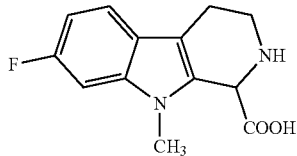
(IVb)

b) Decarboxylation of compound of formula (IVb) under addition of an acid and under heating to 7-fluoro-9-methyl-2,3,4,9-tetrahydro-β-carboline of formula (Vb)

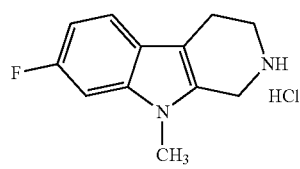
(Vb)

c) Aromatization of 7-fluoro-9-methyl-2,3,4,9-tetrahydro-β-carboline (Vb) to 7-fluoro-9-methyl-β-carboline (Ib) under addition of a catalyst.

The starting material 6-fluoro-1-methyltryptamine hydrochloride is commercially available, for instance from Otavachemicals Ltd. (Vaughan, Kanada). In a preferred embodiment of the invention in step a) a pH-value between 2 and 6, preferably between 3 and 5 and especially preferably a pH-value of 4 is achieved by addition of base. In a further preferred embodiment in step a)' the crystallization of compound IVb is promoted by incubating in ice water.

In a further preferred embodiment the reaction in step b) takes place under inert gas, especially preferred under $N_2$. Furthermore, it is preferred to promote the crystallization of reaction product of step b) by a step b)' incubation at cold, especially preferred between 0° C. and 5° C. for several hours. In a further preferred embodiment for purification of reaction product of step b), a recrystallization from methanol is conducted after crystallization. Furthermore, it is preferred that 7-fluoro-9-methyl-2,3,4,9-tetrahydro-β-carboline in step c) is dissolved in water first and by addition of base, e.g. sodium hydroxide or sodium carbonate, to adjust an alkaline pH-value, especially preferred a pH-value between pH 11 and pH 14, especially preferred pH 13.

In a preferred embodiment the catalyst for oxidative aromatization in step c) may be among others Pd/C, Pt/C, $PdCl_2$, Pd/sepiolite, $Pd/SiO_2$ and $Pd/AlO_4$. Further additives which enable oxidative aromatization are known to the person skilled in the art. However, Pd/C (palladium on carbon, palladium on activated carbon) is preferably used as catalyst.

The bases added in step a) and c) can be independently of each other inorganic or organic bases, e.g. NaOH, KOH, $NH_4OH$, tetraalkylammonium hydroxide, lysine or arginine. The person skilled in the art knows which bases are suitable here for running the reaction. Preferred are however KOH and NaOH, respectively.

The acid added in step b) may be an inorganic or organic acid, e.g. hydrochloric acid, hydrobromic acid, sulfuric acid, phosphoric acid, acetic acid, citric acid, oxalic acid, malic acid, salicylic acid, p-aminosalicylic acid, malonic acid, fumaric acid, succinic acid, ascorbic acid, maleinic acid, sulfonic acid, phosphonic acid, perchloric acid, nitric acid, formic acid, propionic acid, gluconic acid, lactic acid, tartaric acid, hydroxymaleinic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylensulfonic acid, p-toluenesulfonic acid, naphthylsulfonic acid, sulfanilic acid, camphersulfonic acid, china acid, mandelic acid, o-methylmandelic acid, hydrogenebenzenesulfonic acid, picric acid, adipic acid, d-o-tolyltartaric acid, tartronic acid, α-toluic acid, (o-, m-, p-) toluic acid, or naphthylaminesulfonic acid. The person skilled to the art knows which acid is suitable here for running the reaction. However hydrochloric acid is preferred.

It was surprisingly found, that the inventive compound 7-fluoro-9-methyl-β-carboline (Ib) in comparison to already known and tested β-carbolines like 9-methyl-β-carboline shows an increased efficacy on treating of inner ear diseases. Based on recent examinations on the efficacy of 7-fluoro-9-methyl-β-carboline towards the reference substance 9-methyl-β-carboline, the following advantages arise among others:

1. Membrane permeability is increased.
2. Elimination is slowed down (elimination half time of 7F9MβC is approximately 1.5-times higher than of 9MβC).
3. Increased efficacy on active agent induced gene expression of important cellular factors (see examples 4 and 5), which are of significance for cellular regeneration (particularly in the inner ear) after traumas.

Pharmaceutical Applications & Formulations

The compounds according to the invention are especially suitable for treatment of diseases or damages of the inner ear, in particular of the neuronal and sensory structures of the inner ear. These diseases or damages affect herein preferably the hearing and/or the vestibular function. Accompanying symptoms comprise among others hearing damages, hearing loss, dizziness, balance disturbances, tinnitus, disorientation, nausea and vomiting.

Thus, an aspect of the present invention relates to compounds of general formula (I) (or the fluoro-9-methyl-β-carbolines of general formula (I)) for use as medicament. The present invention also relates to compound 6-fluoro-9-methyl-β-carboline for use as medicament. The present invention also relates to compound 7-fluoro-9-methyl-β-carboline for use as medicament. The inventive compounds, in particular the 7-fluoro-9-methyl-β-carboline and the particular preferred 6-fluoro-9-methyl-β-carboline are especially suitable for treatment of diseases and/or damages of the inner ear, in particular labyrinthine deafness. The diseases and/or damages of the inner ear may be preferably acute and chronic diseases of the inner ear. Acoustic trauma, blast injury of the ear, deafness and trauma count to the acute diseases of the inner ear during implantation of inner ear prostheses (insertion trauma). The chronic diseases of the inner ear comprise among others chronic acoustic trauma (labyrinthine deafness by chronic noise exposure), presbyacusis (age-related hearing loss), otosclerosis and Meniere's disease. The term labyrinthine deafness (also defined as cochlear or sensory deafness) comprises deafness due to chronic noise exposure (also defined as chronic labyrinthine deafness or chronic noise trauma) as well as also presbyacusis (age-related hearing loss).

Yet another aspect of the present invention is thus related to a compound of general formula (I), in particular the 7-fluoro-9-methyl-β-carboline and the particularly preferred 6-fluoro-9-methyl-β-carboline for treatment of diseases and/or damages of the inner ear, wherein the diseases and/or damages of the inner ear are acute diseases of the inner ear, selected from the group comprising acoustic trauma, blast injury of the ear, hearing loss and insertion trauma.

Yet another aspect of the present invention is thus related to a compound of general formula (I), in particular the 7-fluoro-9-methyl-β-carboline and the particularly preferred 6-fluoro-9-methyl-β-carboline for treatment of diseases and/or damages of the inner ear, wherein the diseases and/or damages of the inner ear are chronic diseases of the inner ear, selected from the group comprising chronic acoustic trauma, tinnitus and presbyacusis.

Furthermore, the inventive compounds are suitable for treatment of dizziness and balance disturbances caused by hearing damages or ear diseases, and especially caused by damages of the sense of balance in the ear, as well as for increasing the memory, for increasing the learning ability and for increasing the retentiveness, in particular the retentiveness of the short-term memory as well as of the long-term memory.

Diseases and damages of the inner ear may also be triggered by ototoxic substances like antibiotics and/or cytostatic agents. The inventive compounds, in particular the 7-fluoro-9-methyl-β-carboline and the particularly preferred 6-fluoro-9-methyl-β-carboline are suitable for treatment of diseases and/or damages of the inner ear, characterized in that the damages of the inner ear are caused by ototoxic substances. The ototoxic substances are preferably antibiotics and/or cytostatic agents, especially preferred from the group comprising or consisting of: ampicillin, bacampicillin, carbenicillin, indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin, tazobactam, ticarcillin, clavulanic acid, nafcillin, cephalosporin, cefadroxil, cefazolin, cephalexin, cephalothin, cephapirin, cephradin, cefaclor, cefamandol, cefonicid, cefotetan, cefoxitin, cefprozil, ceftmetazol, cefuroxim, ioracarbef, cefdinir, ceftibuten, cefoperazon, cefixim, cefotaxim, cefpodoxim proxetil, ceftazidime, ceftizoxime, ceftriaxon, cefepim, azithromycin, clarithromycin, clindamycin, dirithromycin, erythromycin, roxithromycin, telithromycin, cethromycin, spiramycin, ansymacin, oelandomycin, lincomycin, troleandomycin, cinoxacin, ciprofloxacin, enoxacin, gatifloxacin, grepafloxacin, levofloxacin, iomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, tigecycline, mafenide, silver sulfadiazine, sulfacetamide, sulfadiazine, sulfamethoxazole, sulfasalazine, sulfisoxazole, trimethoprim-sulfamethoxazole, sulfamethizole, rifabutin, rifampin, rifapentin, linezolid, streptogramins, quinopristin, dalfopristin, bacitracin, chloramphenicol, fosfomycin, isoniazide, methenamine, metronidazole, mupirocin, nitrofurantoin, nitrofurazone, novobiocin, polymyxin, spectinomycin, trimethoprim, colistin, cycloserine, capreomycin, ethionamide, pyrazinamide, para-aminosalicylic acid, erythromycin-2'-acetate, erythromycin-2'-stearate, erythromycin estolate, erythromycin ethylsuccinate, erythromycin glutamate, rifampicin, miconazole, ketoconazole, clotrimazole, econazole, bifonazole, butoconazole, fenticonazole, isoconazole, oxiconazole, sertaconazole, sulconazole, tioconazole, fluconazole, itroconazole, isavuconazole, ravuconazole, posaconazole, voriconazole, teraconazole, abfungin, terbinafine, amorolfine, naftifine, butenafine, anidulafungin, caspofungin, micafungin, benzoic acid, ciclopiroxolamine, tolnaftate, 5-fluorocytosine, griseofulvin, haloprogin, fusidic acid, gramicidin, pristinamycin, ramoplanin, tyrothricin, natamycin, rimocidin, filipin, nystatin, amphotericin B, candicine, and hamycin.

Consequently, a further aspect of the present invention is related to a compound of general formula (I), in particular the 7-fluoro-9-methyl-β-carboline and the particularly preferred 6-fluoro-9-methyl-β-carboline for treatment of diseases and/or damages of the inner ear, wherein the damage of the inner ear is caused by ototoxic substances.

A further aspect of the present invention relates to the use of the inventive compounds, in particular the 7-fluoro-9-methyl-β-carboline and the particularly preferred 6-fluoro-9-methyl-β-carboline, for preparation of a medicament for treatment of diseases and/or damages of the inner ear. An embodiment according to the present invention relates to a method for treatment of diseases and/or damages of the inner ear by administration of a compound of general formula (I), preferably of 7-fluoro-9-methyl-β-carboline (Ib) and especially preferably of 6-fluoro-9-methyl-β-carboline (Ia).

Additionally, a further interesting aspect of this invention shall be addressed at this point: We have found in our examinations on cellular level, that the 6-fluoro-9-methyl-β-carboline (6F9MβC) increases the concentration of CREB by a factor of 8 and increases the concentration of BDNF (brain derived neurotrophic factor) up to three times. These insights suggest that the inventive the 6-fluoro-9-methyl-β-carboline (6F9MβC) is not only useful in the treatment of diseases and/or damages of the inner ear, but it also promotes learning and memory.

The underlying mechanisms of learning and memory are very complex. They can be considered on molecular and on cellular level, on the level of system biology and on the level of psychology. One of the key processes for memory formation on molecular level is the activation of the cAMP response element binding proteins (CREB). This leads to new formation of synapses, a process coupled to the memory formation. This process is regulated by many factors. A positive amplification is induced by the brain BDNF and its receptor TRKB. Biobehavioural experiments (see example 9) have shown on the animal model rat that an intraperitoneal administration of inventive 6-fluoro-9-methyl-β-carboline (6F9MβC) in comparison to untreated control animals accelerates learning processes and improves memory.

A further aspect of the present invention is thus related to a compound of general formula (I), in particular the 7-fluoro-9-methyl-β-carboline and the particularly preferred 6-fluoro-9-methyl-β-carboline, for improving learning and memory or for increasing the memory, for increasing the learning ability and for increasing the retentiveness.

An additional aspect of the present invention relates to the use of inventive compounds, in particular the 7-fluoro-9-methyl-β-carboline and the particularly preferred 6-fluoro-9-methyl-β-carboline, for preparation of a pharmaceutical formulation for improving learning and memory. An embodiment of the present invention relates to a method for improving of learning and memory by administration of a compound of general formula (I), preferably of the 7-fluoro-9-methyl-β-carboline (Ib) and particularly preferably of 6-fluoro-9-methyl-β-carboline (Ia).

Yet another aspect of the present invention is thus related to a compound of general formula (I), in particular the 7-fluoro-9-methyl-β-carboline and the particularly preferred 6-fluoro-9-methyl-β-carboline, for improving learning processes and/or memory processes.

A further aspect of the present invention relates to the use of inventive compounds, in particular the 7-fluoro-9-methyl-β-carboline and the particularly preferred 6-fluoro-9-methyl-β-carboline, for preparation of a pharmaceutical formulation for improving learning processes and/or memory processes. An embodiment of the present invention relates to a method for improving of learning processes and/or memory processes by administration of a compound of general formula (I), preferably of the 7-fluoro-9-methyl-β-carboline (Ib) and particularly preferably of 6-fluoro-9-methyl-β-carboline (Ia).

A further aspect of the present invention relates to pharmaceutical compositions in form of droplets, ointments, sprays, liposomes, gels, emulsions or injection solutions containing at least one of the inventive compounds (or at least one compound of general formula (I)).

A further aspect of the present invention relates to pharmaceutical compositions in form of droplets, ointments, sprays, liposomes, gels, emulsions or injection solutions containing one or more of the inventive compounds (or one or more compounds of general formula (I)).

Yet another aspect of the present invention relates to pharmaceutical compositions in form of droplets, ointments, sprays, liposomes, gels, emulsions or injection solutions containing 6-fluoro-9-methyl-β-carboline.

A further aspect of the present invention relates to pharmaceutical compositions in form of droplets, ointments, sprays, liposomes, gels, emulsions or injection solutions containing 7-fluoro-9-methyl-β-carboline.

Yet another aspect of the present invention relates to pharmaceutical compositions in form of droplets, ointments, sprays, liposomes, gels, emulsions or injection solutions containing 6-fluoro-9-methyl-β-carboline and 7-fluoro-9-methyl-β-carboline.

Therefore, the present invention relates also to pharmaceutical compositions in form of droplets, ointments, sprays, liposomes, gels, emulsions or injection solutions containing 6-fluoro-9-methyl-β-carboline and/or 7-fluoro-9-methyl-β-carboline.

Further, the present invention relates also to pharmaceutical compositions, which are prepared using at least one of the inventive compounds (or at least one compound of general formula (I)) or a salt thereof.

Also, the present invention relates to pharmaceutical compositions, which are prepared using one or more of the inventive compounds (or one or more compounds of general formula (I)) or salts thereof.

Also, the present invention relates to pharmaceutical compositions, which are prepared using the inventive compound 7-fluoro-9-methyl-β-carboline or a salt thereof.

Further, the present invention relates to pharmaceutical compositions, which are prepared using the inventive compound 6-fluoro-9-methyl-β-carboline or a salt thereof.

The present invention also relates to pharmaceutical compositions, which are prepared using the inventive compound 6-fluoro-9-methyl-β-carboline or a salt thereof and using the inventive compound 7-fluoro-9-methyl-β-carboline or a salt thereof.

Likewise, the present invention relates to pharmaceutical compositions, which are prepared using the inventive compound(s) 6-fluoro-9-methyl-β-carboline and/or 7-fluoro-9-methyl-β-carboline or salts thereof.

Besides at least one compound of the present invention (or one compound of general formula (I)), in particular besides the 7-fluoro-9-methyl-β-carboline and besides the particularly preferred 6-fluoro-9-methyl-β-carboline, the pharmaceutical compositions contain preferably a pharmacologically acceptable carrier, adjuvant and/or solvent.

Besides the 6-fluoro-9-methyl-β-carboline of the present invention the pharmaceutical compositions contain preferably a pharmacologically acceptable carrier, adjuvant and/or solvent The pharmaceutical compositions containing inventive compound may be prepared and administered in form of transdermal application systems (plaster, film), droplets, pills, tablets, film tablets, layer tablets, dragees, gels, hydrogels, ointments, sirups, granulates, suppositories (uvulas), emulsions, dispersions, microcapsules, capsules, microformulations, nanoformulations, liposomes, powders, sprays, aerosols, solutions, juices, suspensions, infusion solutions or injection solutions. Preferred are pharmaceutical compositions in form of liposomes, gels and emulsions. Especially preferred are hydrogel formulations.

Such compositions are among others suitable for inhalation or intravenous, intraperitoneal, intramuscular, subcutaneous, mucocutaneous, oral, rectal, transdermal, topical, buccal, intradermal, intragastral, intracutaneous, intranasal, intrabuccal, percutaneous, intratympanal or sublingual administration. Especially preferred is the administration or injection into the middle ear as well as the topical administration on to the ear drum.

As pharmaceutically acceptable carrier may be used for example lactose, starch, sorbitol, sucrose, cellulose, magnesium stearate, dicalcium phosphate, calcium sulfate, talc, mannitol, ethyl alcohol and the like. Powders as well as tablets can consists of 5 to 95 wt % of such a carrier.

Furthermore, exploders, dyes, flavors and/or binders can be added to the pharmaceutical compositions Liquid formulations comprise solutions, suspensions, sprays and emulsions. For example injection solutions based on water or based on water-propylene glycol for parenteral injections. For preparation of suppositories preferably low-melting waxes, fatty acid esters and glycerides are used.

Capsules are for instance prepared from methylcellulose, polyvinyl alcohols or denaturate gelatine or starch. As exploders can be used starch, sodium carboxymethyl starch, natural and synthetic gums like for instance carob gum, karaya gum, guar gum, tragacanth gum and agar as well as cellulose derivatives like methylcellulose, sodium carboxymethylcellulose, microcrystalline cellulose as well as alginates, clays and bentonites. These components may be used in quantities of 2 to 30 wt %.

As binders can be added sugar, starch from corn, rice or potatoes, natural as well as synthetic gums like acacia gum or guar gum, gelatine tragacanth gum, alginic acid, sodium alginate, ammonium calcium alginate, methylcellulose, sodium carboxymethylcellulose, hydroxypropyl methylcellulose, polyvinylpyrrolidone, polyethylene glycol, waxes as well as inorganic compounds like magnesium aluminum silicates. The binders can be added in quantities of 1 to 30 wt %.

As lubricants may be used stearates like magnesium stearate, calcium stearate, potassium stearate, stearic acid, high-melting waxes as well as water-soluble lubricants like sodium chloride, sodium benzoate, sodium acetate, sodium oleate, polyethylene glycol, boric acid and amino acids like leucine. Such lubricants can be used in quantities of 0.05 to 15 wt %.

Thus, all pharmaceutical formulations are preferred, which are suitable for administering the active agent locally on the round window membrane. Furthermore, it is preferred, when the pharmaceutical formulations contain a membrane penetration promoter, which supports the passage of the inventive compound of general formula (I), in particular of 7-fluoro-9-methyl-β-carboline and of particularly preferred 6-fluoro-9-methyl-β-carboline, through the round window membrane. Accordingly, liquid or gel-type formulations are especially preferred. Of course it is also possible to administer the active agent orally.

Pharmaceutical compositions for any type of administration of compounds of general formula (I) contain a for the therapeutic effect adequate amount of compound(s) of general formula (I) and, if necessary, inorganic or organic, solid or liquid pharmaceutically acceptable carrier substances. Pharmaceutical compositions which are suitable for a topical administration in the middle ear, contain aqueous solutions or suspensions, which can be prepared before administration in the middle ear, for instance in the case of lyophilized formulations that contain compound(s) of general formula (I) only or possibly together with a carrier.

Pharmaceutical compositions for any type of administration of 7-fluoro-9-methyl-β-carboline contain a for the therapeutic effect adequate amount of 7-fluoro-9-methyl-β-carboline and, if necessary, inorganic or organic, solid or liquid pharmaceutically acceptable carrier substances. Pharmaceutical compositions which are suitable for a topical administration in the middle ear, contain aqueous solutions or suspensions, which can be prepared before administration in the middle ear, for instance in the case of lyophilized formulations that contain 7-fluoro-9-methyl-β-carboline only or together with a carrier.

Pharmaceutical compositions for any type of administration of 6-fluoro-9-methyl-β-carboline contain a for the therapeutic effect adequate amount of 6-fluoro-9-methyl-β-carboline and, if necessary, inorganic or organic, solid or liquid pharmaceutically acceptable carrier substances. Pharmaceutical compositions which are suitable for a topical administration in the middle ear, contain aqueous solutions or suspensions, which can be prepared before administration in the middle ear, for instance in the case of lyophilized formulations that contain 6-fluoro-9-methyl-β-carboline only or together with a carrier.

The pharmaceutical compositions further comprise gels that are biodegradable or non-biologically degradable, aqueous or non-aqueous or based on microspheres. Examples for such gels include polyoxameres, hyaluronates, xyloglucanes, chitosanes, polyester, polyactides, polyglycolides or their co-polymers PLGA, saccharoseacetate isobutyrate and glycerine monooleate. Pharmaceutical compositions, which are suitable for a enteral or parenteral administration, contain tablets or gelatine capsules or aqueous solutions or suspensions as described above.

The pharmaceutical compositions can be sterilized and/or can contain adjuvant, for instance preservatives, stabilizers, humectants and/or emulsifiers, salts for regulating the osmotic pressure and/or buffer. The pharmaceutical compositions according to the invention may contain further active agents, if desired. These pharmaceutical compositions can be prepared by any kind of method known from prior art, for instance by conventional methods like mixing, granulating, confectioning, dissolving and lyophilizing and they can contain approximately 0.01 to 100 wt %, preferably between 0.1 and 50 wt %, for lyophilisates up to 100 wt % of 6-fluoro-9-methyl-β-carboline. These pharmaceutical compositions can also contain approximately from 0.01 to 100 wt %, preferably between 0.1 and 50% wt, for lyophilisates up to 100 wt % 7-fluoro-9-methyl-β-carboline. These pharmaceutical compositions can also contain approximately from 0.01 to 100 wt %, preferably between 0.1 and 50% wt, for lyophilisates up to 100 wt % compounds of general formula (I).

In a preferred embodiment the pharmaceutical composition according to the invention is formulated for a topical administration. Suitable carrier for an otogenic administration are organic and inorganic substances that are pharmaceutically acceptable and do not react with a compound according to the invention and/or its further active agents, for instance cooking salt, alcohols, vegetable oils, benzyl alcohols, alkyl glycols, polyethylene glycols, glycerine triacetate, gelatine, carbohydrates like lactose or starch, magnesium carbonate (magnesia, chalk), stearate (waxes), talc and petrolatum (vaseline). The described compositions can be sterilized and/or can contain adjuvants like lubricants, preservatives like thiomersal (i.e. 50 wt %), stabilizers and/or humectants, emulsifiers, salts for influencing the osmotic pressure, buffer substances, dyes and/or flavors. These compositions may also contain one or multiple additional active agents, if necessary.

Otogenic compositions according to the invention may comprise different compounds and/or substances, for instance other bioactive substances like antibiotics, anti-inflammatory active agents like steroids, cortisones, analgesics, antipyrines, benzocaines, procaines.

Compositions according to the present invention for topical administration can contain other pharmaceutically acceptable compounds and/or substances. In a preferred embodiment of the present invention a topical excipient is selected, which does not amplify the release of compounds of general formula (I), in particular of 7-fluoro-9-methyl-β-carboline and of particularly preferred 6-fluoro-9-methyl-β-carboline, and of the possibly additional active agent or active agents to the blood circular system or to the central nervous system, when it is administered at the ear, in the middle ear or in the auditory canal. Possible carrier substances contain hydrocarbonic acids, water-free adsorbents like hydrophile petrolatum (vaseline) and water-free lanolin (i.e. Aquaphor®) and means based on water—oil emulsions like lanolin and Cold Cream. More preferred are carrier substances that essentially are non-excluding and that contain usually carrier substances, which are water soluble as well as substances based on oil-in-water emulsions (creams or hydrophilic ointments) and substances with a water-soluble basis like carrier substances based on polyethylene glycol and aqueous solutions that were gelled with several substances like methylcellulose, hydroxyethylcellulose and hydroxypropylmethylcellulose.

For oral administration in form of tablets or capsules a compound according to the invention can be mixed with non-toxic pharmaceutically acceptable adjuvants, selected from the list comprising binders like pre-gelled corn starch, polyvinylpyrrolidone or hydroxypropylmethylcellulose; fillers like lactose, saccharose, glucose, mannitol, sorbitol and other reducing and non-reducing sugars, microcrystalline cellulose, calcium sulfate, calcium hydrogenphosphate; lubricants like magnesium stearate, talc or silica, stearic acid, sodium stearylfumarate, glyceryl behenate, calcium stearate and likewise; disintegrants like potato starch or sodium glycolate starch; humectants like sodium dodecylsulfate; dyes; flavors; gelatine; sweeteners; natural and synthetic gums like gum arabic, tragacanth gum or alginates; buffer salts; carboxymethylcellulose; polyethylene glycol; waxes and likewise The tablets can be coated by a concentrated sugar solution, which for instance can contain gum arabic, gelatine, talc, titanium oxide and likewise. In another embodiment the tablets can be coated by a polymer that dissolves in a volatile organic solvent or in a mixture of organic solvents. In a preferred embodiment the inventive compounds of general formula (I), in particular 7-fluoro-9-methyl-β-carboline and particularly preferred 6-fluoro-9-methyl-β-carboline, are formulated as tablet for immediate release or as tablet in slow-release form. Dosage forms for immediate release allow the release of the majority or the total amount of a compound of general formula (I) within a short period time like 60 minutes or less and enable rapid absorption of the compound according to the invention. Slow-release forms allow the retarded release over a longer period of time in order to reach a therapeutically active plasma level of a compound of general formula (I) and/or to keep this therapeutically active plasma level constant over a longer period of time and/or to modify other pharmacokinetic properties of compounds of general formula (I), in particular of 7-fluoro-9-methyl-β-carboline and of particularly preferred 6-fluoro-9-methyl-β-carboline.

A compound according to the invention can be blended for instance with a vegetable oil or polyethylene glycol for formulating soft gelatine capsules. Hard gelatine capsules can contain an inventive compound in granular form using either above mentioned adjuvants for tablets like lactose, saccharose, mannitol, starches like potato starch, corn starch or amylopectine, cellulose derivatives or gelatine. Also liquid or semi-liquid forms of a compound according to the invention can be filled into hard gelatine capsules.

The compounds according to the invention of general formula (I), in particular 7-fluoro-9-methyl-β-carboline and particularly preferred 6-fluoro-9-methyl-β-carboline, can also be incorporated in microbeads or microcapsules that are prepared from polyglycolic acid/lactic acid (PGLA) for instance. Biocompatible polymers selected from the list comprising polylactic acid, polyglycolic acid, copolymers of polylactic acid and polyglycolic acid, poly-ε-caprolactone, polyhydroxybutyric acid, polyorthoester, polyacetals, polyhydropuranes, polycyanoacrylates and cross-linked or amphipathic block copolymers of hydrogels, can be used for achieving a controlled release of an inventive compound from pharmaceutical compositions of the present invention.

In a further embodiment of the invention compounds of general formula (I), in particular 7-fluoro-9-methyl-β-carboline and particularly preferred 6-fluoro-9-methyl-β-carboline, are provided as a liquid formulation for oral administration. Liquid preparations for oral administration can be provided in form of solutions, syrups, emulsions or suspensions. Alternatively, liquid formulations for oral administration can be prepared by reconstitution of the dry formulation for oral administration with water or another suitable carrier substance before the application. Preparations for oral administration can be formulated so that a controlled and retarded release of a compound according to the invention and possibly additional active agents can be achieved.

For oral administration in liquid form a compound according to the invention can be used with non-toxic pharmaceutically acceptable inert carrier substances like ethanol, glycerin, water; suspension agents like sorbitol syrup, cellulose derivatives or hardened edible fats; emulsifiers like lecithin or gum Arabic; non-aqueous carrier substances like almond oil, oily esters, ethanol or fractioned vegetable oils; preservatives like methyl or propyl p-hydroxybenzoates or sorbic acid; and likewise.

Stabilizers like for instance antioxidants like butylhydroxyanisole, butylhydroxytoluene, propyl gallate, sodium ascorbate, citric acid can also be used for stabilization of the dosage form. For example, the solutions of a compound according to the invention can contain approximately 0.2 wt % until approximately 20 wt %, wherein the levelling compound can be sugar and a mixture of ethanol, water, glycerin and propylene glycol. Optionally, these liquid formulations can contain dyes, flavors, saccharine, carboxycellulose as thickener and/or other adjuvants.

In a further embodiment, a therapeutically active dose of a compound according to the invention is administered orally by a solution, wherein the solution may contain a preservative, sweetener, solubilizer and a solvent. The solution for oral administration may contain one or more buffers, flavors or further excipients. In a further embodiment peppermint or another flavor is added to the solution of the inventive compound for oral administration.

For administration by inhalation, a compound according to the present invention can be administered in a suitable way, like in a dosage form of an aerosol spray with pressurized packs or a sprayer using a suitable propellant like dichlorofuoromethane, trichlorofluoromethane, dichlorotetrafluoroethane, carbon dioxide or another suitable gas. When using a pressurized aerosol the dose can be determined by providing a valve for administration of a measured quantity. Capsules and cartridges of for example gelatine for use in inhalers or insufflators can be formulated so that the capsules and cartridges contain a powder mixture of the compound according to the invention and possibly one or more further active agents as well as a suitable powder base substance like lactose or starch.

Solutions for parenteral administration by injection can be prepared from an aqueous solution of a water-soluble pharmaceutically acceptable salt of a compound according to the invention, in particular of 7-fluoro-9-methyl-β-carboline and of particularly preferred 6-fluoro-9-methyl-β-carboline, with a concentration of approximately 0.5 wt % to 10 wt %. These solutions can also contain stabilizers and/or buffer substances and can in a suitable manner provided as ampoules with different dose units.

Thus, the herein presented inventive compounds, in particular 7-fluoro-9-methyl-β-carboline and particularly preferred 6-fluoro-9-methyl-β-carboline, are useful for the preparation of pharmaceutical compositions for treatment of diseases and/or damages of the inner ear. Here the diseases and/or damages of the inner ear are preferably acute and/or chronic diseases of the inner ear. Acoustic trauma, blast injury of the ear, hearing loss and insertion trauma belong among others to the acute diseases of the inner ear. Chronic acoustic trauma, tinnitus and presbyacusis belong to the chronic diseases of the inner ear. The diseases and/or damages can furthermore be characterized by the fact that they may be caused by ototoxic substances.

DESCRIPTION OF FIGURES

FIGS. 2 and 3: show the culture of human neuroblastoma cells (SH-SY5Y) that are for 15 days exposed to increasing concentrations of 6-fluoro-9-methyl-β-carboline (AC102) (FIG. 2). For comparison the effect of 9-methyl-β-carboline (AC102) under the same conditions is presented in FIG. 3. The upper row comes from the current experiment with 70 μmol/L, while the lower row shows concentration dependency from an earlier experiment. The compound according to the invention (AC102) inhibits proliferation of cells and induces sprouting of slim extensions as well as a change in size and shape of the cells. This is explained by induction of a differentiation. This effect of the compound is especially pronounced when concentrations 0 μM (reference) and 30 μM are compared at both times.

EXAMPLES

Example 1a

Synthesis of 6-fluoro-9-methyl-β-carboline

Figure 1:
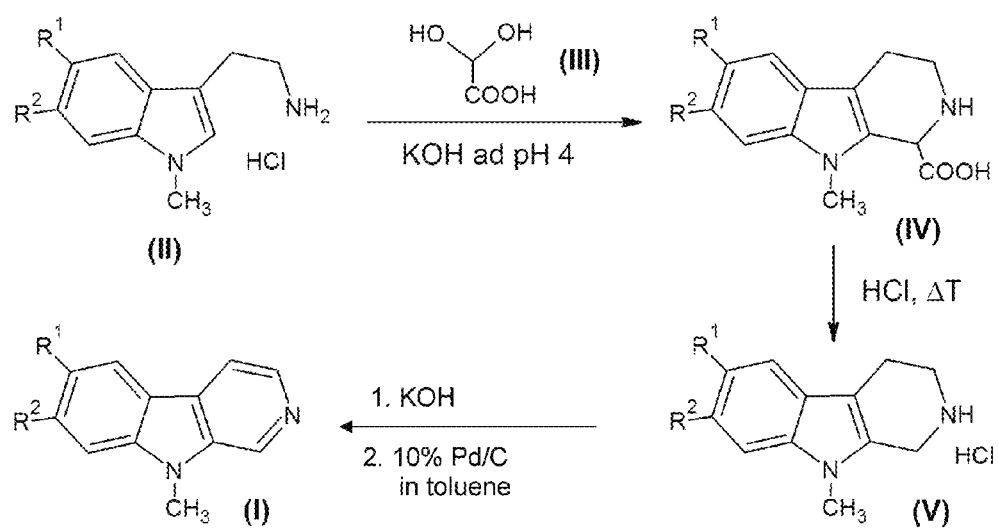
FIG. 1: Reaction scheme of three-step reaction of a fluoro-1-methyltryptamine (as hydrochloride) of general formula (II) and gloxylic acid hydrate (III) over the intermediate product of general formula (IV) and a fluoro-9-methyl-2,3,4,9-tetrahydro-β-carboline of general formula (V) to a fluoro-9-methyl-β-carboline of general formula (I). Herein applies either $R^1$=—F and $R^2$=—H or —F and this applies equally to compounds of general formula (I), (II), (IV) and (V), or R$^1$=—H and R$^2$=—F and this applies equally to compounds of general formula (I), (II), (IV) and (V).
Figure 1A:
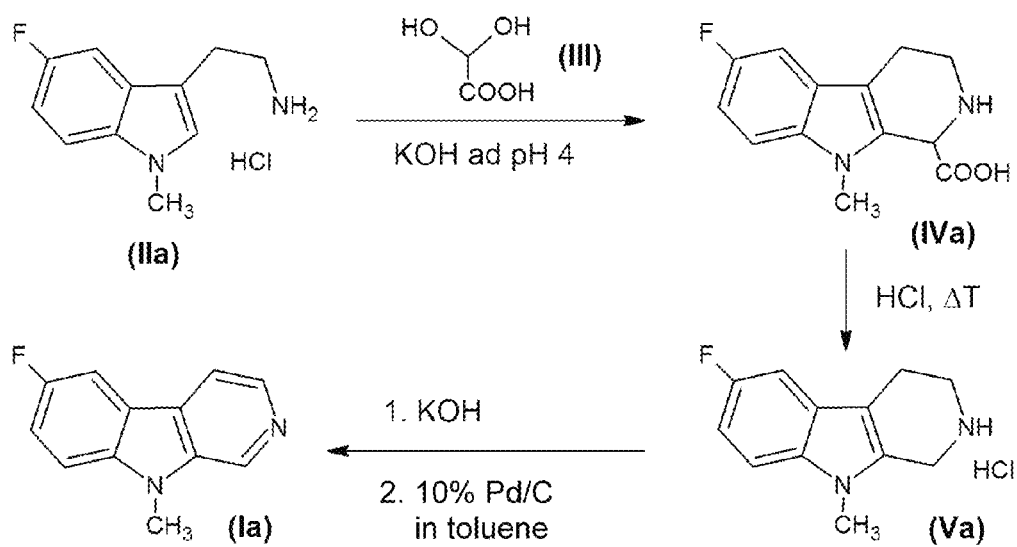
FIG. 1a: Reaction scheme of three-step reaction of 5-fluoro-1-methyltryptamine hydrochloride (IIa) and gloxylic acid hydrate (III) over the intermediate product (IVa) and 6-fluoro-9-methyl-2,3,4,9-tetrahydro-β-carboline (Va) to 6-fluoro-9-methyl-β-carboline (Ia).

Analogous to procedure of Ho and Walker (Beng T. Ho and K. E. Walker; *Org. Synth.* 1971, 51, 136 or *Org. Synth.* 1988, *Coll. Vol.* 6, 965), in 10 mL water are dissolved 3.5 mmol (800 mg) 5-fluoro-1-methyltryptamine hydrochloride (FIG. 1a, Formula IIa, AKos GmbH, Steinen) and combined with a solution of 3.9 mmol (356.4 mg) glyoxylic acid hydrate (FIG. 1a, Formula III) in 810 μL water. Then, a solution of 3.4 mmol (190.4 mg) potassium hydroxyide is pipetted whilst stirring, wherein the pH is adjusted to approximately 4. The reaction mixture is stirred 3 h at room temperature and for completion of crystallization placed into an ice bath for a further hour. The orange beige precipitate of the betaine (FIG. 1a, Formula IVa) is filtered off and washed with little ice water. For decarboxylation the still wet filter cake of the betaine (FIG. 1a, Formula IVa) is transferred into a flask and dissolved in diluted hydrochloric acid (6.48 mL water and 918 μL concentrated hydrochloric acid). The reaction mixture is refluxed 10 min under nitrogen, again 945 μL concentrated hydrochloric acid is added through a septum and again refluxed for 15 min. Subsequently, the solution is brought to room temperature and stored 2 h at 0-5° C. The formed crystals of 6-fluoro-9-methyl-2,3,4,9-tetrahydro-β-carboline (FIG. 1a, Formula Va) are filtered off and recrystallized from methanol. Yield: 230 mg (52%).

For aromatization, in 15 mL water are dissolved 230 mg 6-fluoro-9-methyl-2,3,4,9-tetrahydro-β-carboline (FIG. 1a, Formula Va), set to pH 13 with sodium hydroxide and extracted three times with a mixture of ethyl acetate and toluene (1:1). The combined organic phases are dried over magnesium sulfate ($MgSO_4$) and evaporated under reduced pressure. The oily residue is taken up with 50 mL toluene, combined with 100 mg Pd/C (10%) and refluxed for 24 h. Pd/C is filtered from the still warm solution and the filter cake is washed with 20 mL warm toluene. The organic phase is evaporated in vacuum. The oily residue of 6-fluoro-9-methyl-β-carboline (FIG. 1a, Formula Ia) crystallizes during standing and forms 183 mg (96%) mustard-yellow crystals.

melting point: 117-118° C., GC/MS of the free base: m/z=201 (10%), 200 (100%), 199 (71%), 185 (13%), 145 (6%), 131 (6%), $^1$H-NMR: δ (ppm) methanol d4, 400 MHz: 3.80, s, 3H, N—$CH_3$; 7.34, m, $^1$H; 7.43, m, $^1$H; 7.73, m, $^1$H; 7.91, m, $^1$H; 8.24, m, $^1$H; 8.73, m, $^1$H, $^{13}$C-NMR: δ (ppm) methanol d4, 100 MHz: 28.23; 106.38; 106.64; 110.20 and 110.29, d; 114.67; 116.25; 116.52; 120.59 and 120.66, d; 127.91; 131.30; 136.95; 137.51; 138.35; 156.20 and 158.55, d, elemental analysis for $C_{12}H_9FN_2 \times 0.1\ H_2O \times 0.1$ toluene: C, H, N, calculated: C, 72.21; H, 4.77; N, 13.26. found: C, 72.01; H, 4.55; N, 13.45.

Example 1b

Synthesis of 7-fluoro-9-methyl-β-carboline

Figure 1B:
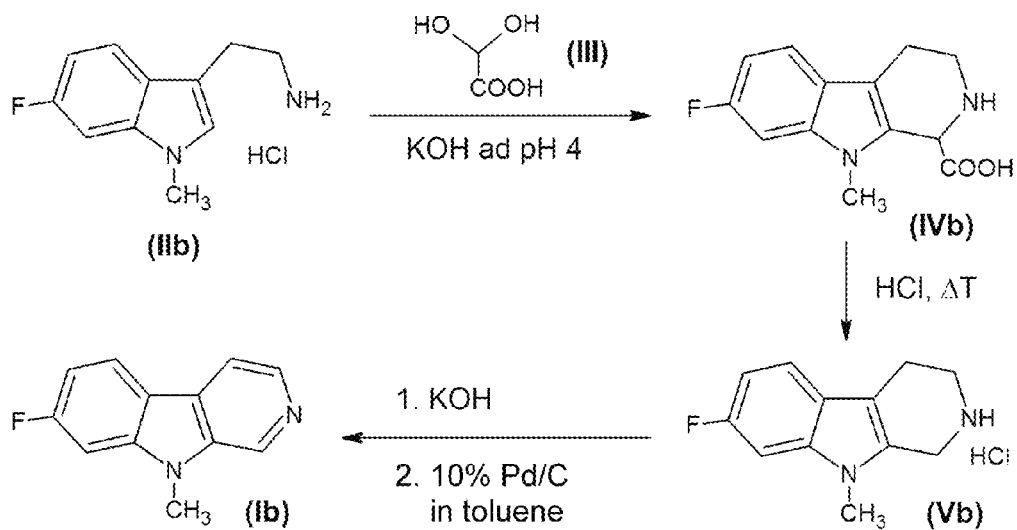
FIG. 1b: Reaction scheme of three-step reaction of 6-fluoro-1-methyltryptamine hydrochloride (IIb) and gloxylic acid hydrate (III) over the intermediate product (IVb) and 7-fluoro-9-methyl-2,3,4,9-tetrahydro-β-carboline (Vb) to 7-fluoro-9-methyl-β-carboline (Ib).
Figure 2:
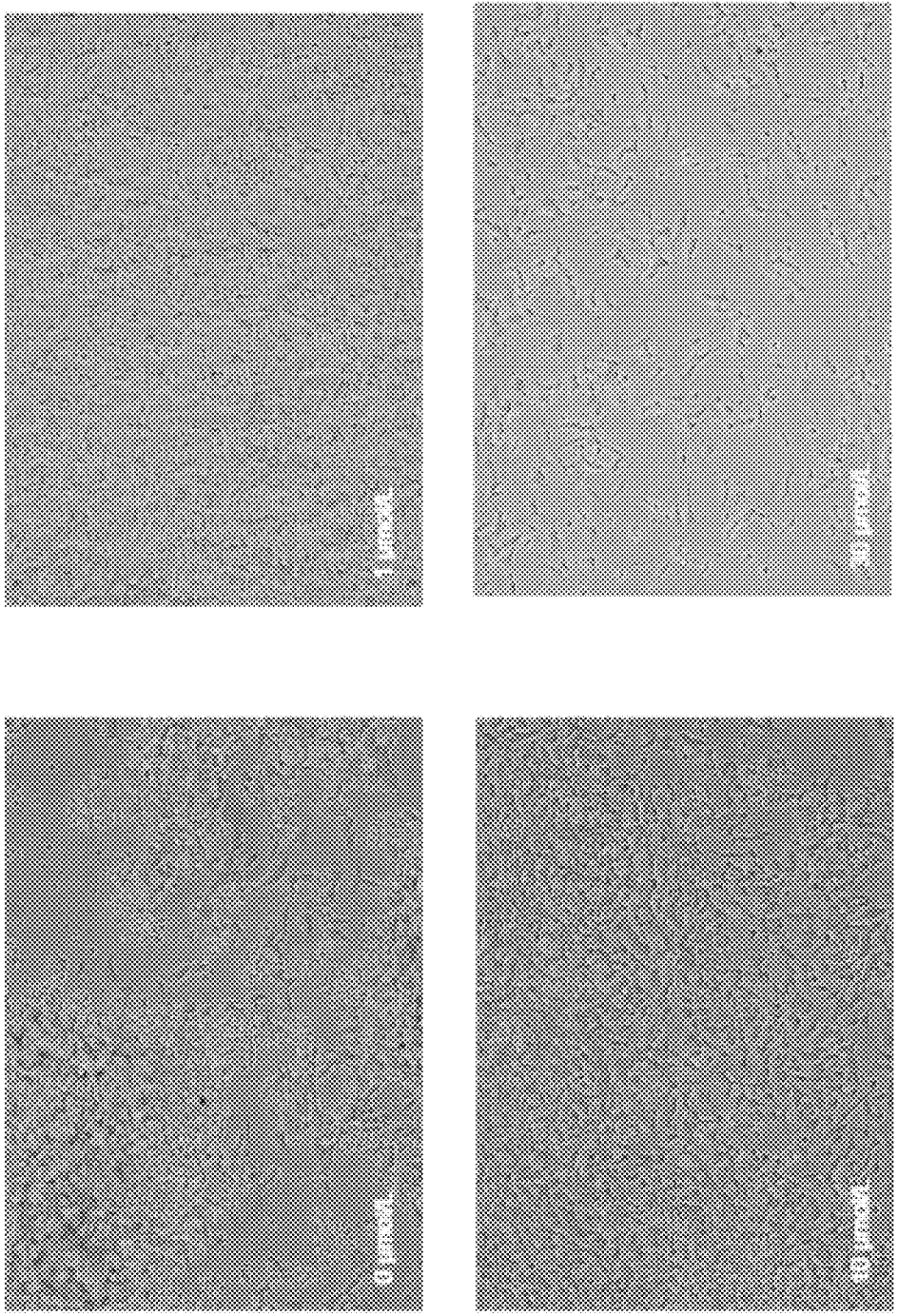
FIG. 2: SH-SY5Y cell line 15 days incubation with AC102 (6-fluoro-9-methyl-β-carboline)
Figure 3:
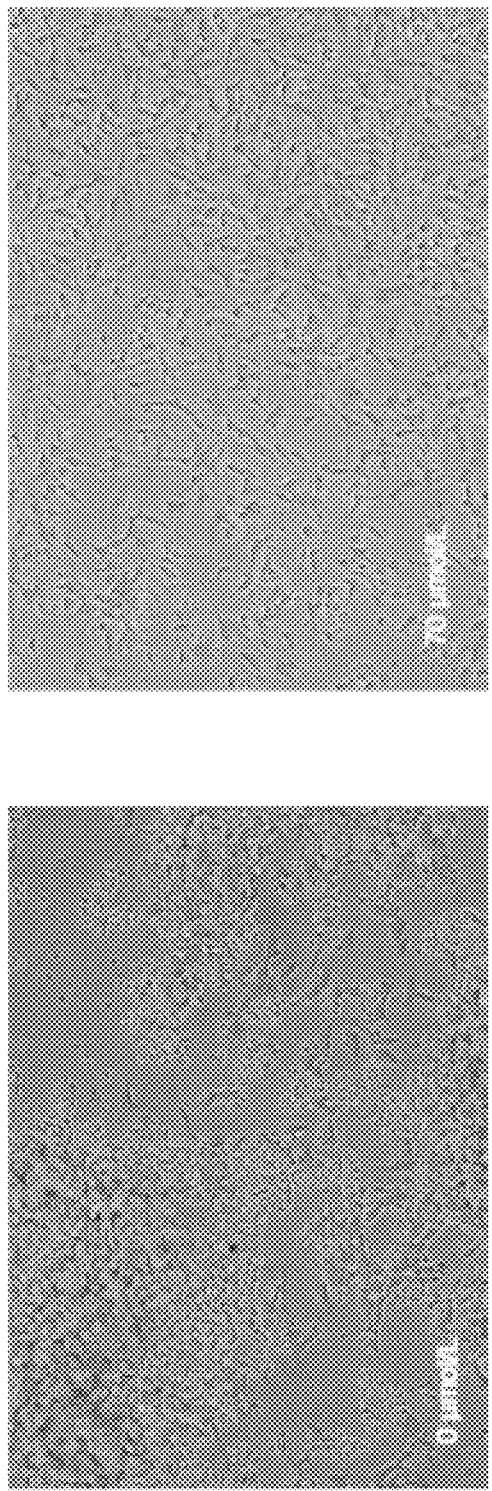
FIG. 3: SH-SY5Y cell line 15 days incubation with AC002 (9-methyl-β-carboline)
Figure 3:
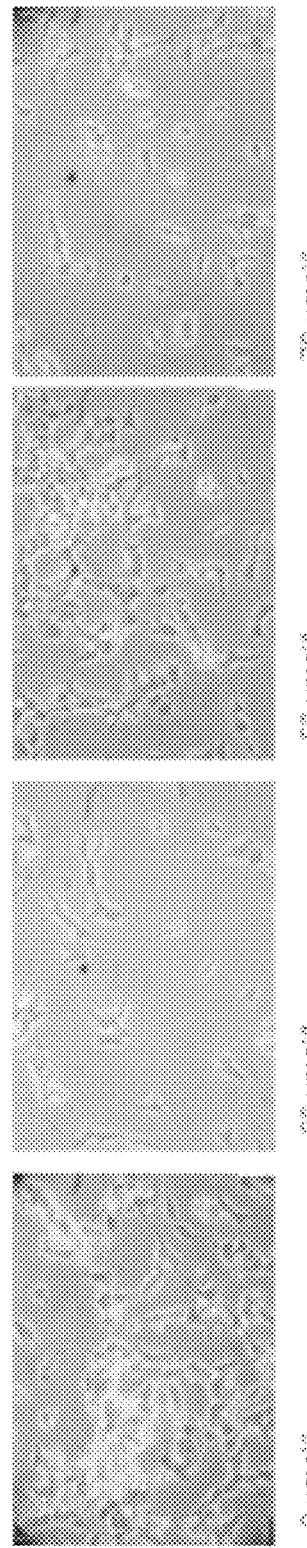

Analogous to synthesis of 6-fluoro-9-methyl-β-carboline, in 10 mL water are dissolved 3.5 mmol (800 mg) 6-fluoro-1-methyltryptamine hydrochloride (FIG. 1b, Formula IIb, Otavachemicals Ltd., Vaughan, Canada) and combined with a solution of 3.9 mmol (356.4 mg) glyoxylic acid hydrate (FIG. 1b, Formula III) in 810 μL water. Then, a solution of 3.4 mmol (190.4 mg) potassium hydroxyide is pipetted whilst stirring, wherein the pH is adjusted to approximately 4. The reaction mixture is stirred 3 h at room temperature and for completion of crystallization placed into an ice bath for a further hour. The orange-beige precipitate of the betaine (FIG. 1b, Formula IVb) is filtered off and washed with little ice water. For decarboxylation the still wet filter cake of the betaine (FIG. 1b, Formula IVb) is transferred into a flask and dissolved in diluted hydrochloric acid (6.48 mL water and 918 μL concentrated hydrochloric acid). The reaction mixture is refluxed 10 min under nitrogen, again 945 μL concentrated hydrochloric acid is added through a septum and again refluxed for 15 min. Subsequently, the solution is brought to room temperature and stored 12 h at 0-5° C., wherein 7-fluoro-9-methyl-2,3,4,9-tetrahydro-β-carboline (FIG. 1b, Formula Vb) precipitates as HCl-salt. The formed crystals are filtered off and recrystallized from methanol. Yield: 1 mmol and 250 mg (28%), respectively.

For aromatization, in 15 mL water are dissolved 250 mg 7-fluoro-9-methyl-2,3,4,9-tetrahydro-β-carboline×HCl (FIG. 1b, Formula Vb), set to pH 13 with diluted potassium hydroxide solution and stored in the fridge over night. The free base crystallizes as beige, crystalline solid that is filtered off, washed with water and dried in vacuum. The solid is suspended in 50 mL toluene, combined with 100 mg Pd/C (10%) and refluxed 8 h (TLC for conversion control). Pd/C is filtered from the still warm solution and the filter cake is washed with 20 mL warm toluene. The organic phase is evaporated in vacuum. The oily residue of 7-fluoro-9-methyl-β-carboline (FIG. 1b, Formula Ib) crystallizes during standing and forms mustard-yellow crystals, which are purified by column chromatography ($CHCl_3$/methanol 9:1). There remain 160 mg (80%).

Example 2

Differentiation of Human Neuroblastoma Cells (SH-SY5Y)

The SH-SY5Y cell line was obtained from the German collection of microorganisms and cell cultures—DSMZ, Braunschweig. The cells were cultivated in MEM (Minimum essential medium, Life Technologies) with 10% FCS (fetal calf serum, Biochrom AG) and penicillin/streptomycin (Biochrom AG). For morphological examinations the cells were seeded in a density of $1.5 \times 10^4$ cells/$cm^2$ in 24-well plates (Falcon, cell culture treated) with 1 mL medium. A stock solution of 10 mmol/L of the compound according to the invention 6-fluoro-9-methyl-β-carboline was prepared in 50% ethanol and sterile filtered. Five hours after seeding of the cells the compound according to the invention 6-fluoro-9-methyl-β-carboline was added in the corresponding amount to the medium achieving the desired final concentration. The medium was changed once a week. The cells were regularly microscopically examined. Microscopic images were taken at BZ Keyence 10 with a 10×lens and 4×digital zoom. An automatic contrast enhancement was made with the program BZ Analyzer.

The findings give an advantage of the inventive compound 6-fluoro-9-methyl-β-carboline compared with 9-methyl-β-carboline, because a comparable differentiation of the tested cells is observed at first at a concentration of approximately 70 μM 9-methyl-β-carboline in comparison to 30 μM 6-fluoro-9-methyl-β-carboline. 50 μM 9-methyl-β-carboline resulted in a too low neurite growth, as indication of a differentiation of human neuroblastoma cells, compared to 30 μM of the inventive compound 6-fluoro-9-methyl-β-carboline.

Example 3

Lipophilicity of 6-fluoro-9-methyl-β-carboline in comparison to 9-methyl-β-carboline The following experiments were conducted to examine, if the lipophilicity of 6-fluoro-9-methyl-β-carboline is higher than the lipophilicity of 9-methyl-β-carboline.

Figure 4:
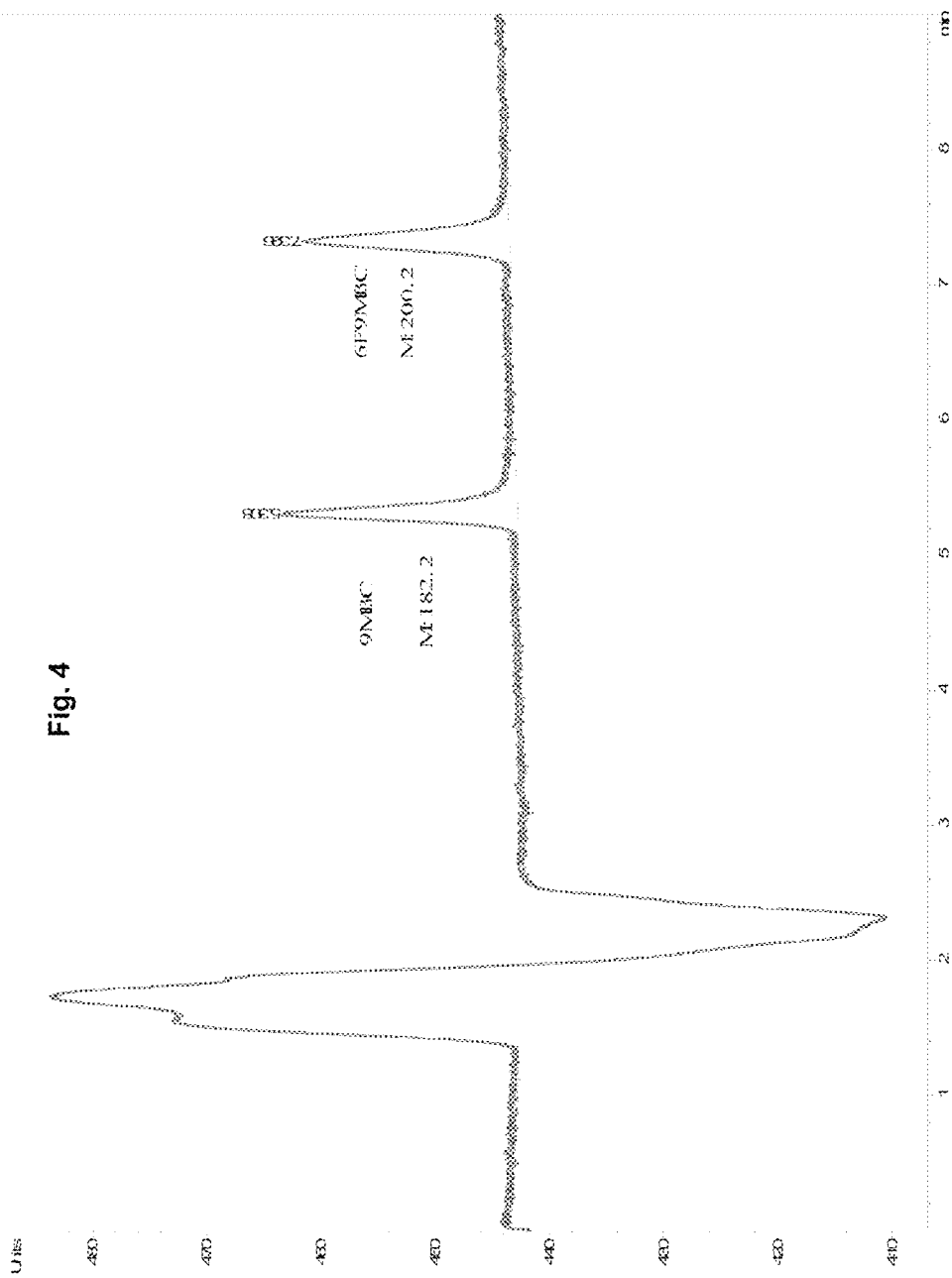
FIG. 4: HPLC chromatogram of 9-methyl-β-carboline (9MβC, AC002) and 6-fluoro-9-methyl-β-carboline (6F9MβC, AC102). Retention times are 5.3 and 7.3 min, respectively. Column: Phenomenex Luna 3uC18 (2) 100A; eluent: ACN90%/NH$_4$Ac 40 mM [45/55]

Experimentally, the lipophilicity is determined by either actual distribution between octanol and water or more easily, as described by Valkó, by HPLC experiments with reversed-phase columns (RP18) (K. Valkó; *Journal of Chromatography A* 2004, 1037 (1-2), 299-310). Herein the components of the substance to investigate interact differently strong with the stationary phase. If the interaction of a component with the stationary phase is weaker, then it exits the column earlier. Depending on the strength of these interactions the components of the substance appear at different times (at retention times) at the end of the separation column. Such experiments were conducted with both substances. It was shown, that the inventive compound 6-fluoro-9-methyl-β-carboline has a longer retention time than 9-methyl-β-carboline (FIG. 4), which indicates clearly a higher lipophilicity of 6-fluoro-9-methyl-β-carboline regarding the selected column as well as stationary phase.

Furthermore, the solubility of both compounds in water was determined by preparing concentration series of both compounds in water at room temperature. The concentration at which the compound was barely soluble was determined by external calibration. The corresponding concentration was quantified by HPLC. It was found that 6-fluoro-9-methyl-β-carboline (base) has a maximally soluble concentration of 29.7 mg/L and 9-methyl-β-carboline (base) has a maximally soluble concentration of 168.3 mg/L. The lower water solubility of 6-fluoro-9-methyl-β-carboline supports in reverse the increased lipophilicity compared to 9-methyl-β-carboline.

The lipophilicity of a compound has a strong effect on ist ADME parameters ("absorption", "distribution", "metabolism", and "excretion"). Due to the increased lipophilicity, compounds are especially enriched in lipophilic compartments. To pass membranes, chemical substances must pass the hydrophobic part of a biologic double membrane, thus they must be lipophilic. There is often a good correlation between lipid solubility and membrane passage. Therefore the lipophilicity has a significant influence one the pharmacokinetics of a compound. Summarized, multiple experiments show a significantly increased lipophilicity of 6-fluoro-9-methyl-β-carboline compared to 9-methyl-β-carboline.

A further important aspect of the compound according to the invention relates the extension of elimination half time. While 9-methyl-β-carboline is degraded by hydroxylation at position 6 with subsequent conjugation reaction, for 6-fluoro-9-methyl-β-carboline this metabolic pathway is blocked by the fluoride group. This is probably the reason for an increasing of the half time of 6-fluoro-9-methyl-β-carboline compared to 9-methyl-β-carboline. Because the half time of Harman, a structural analogue of 9-methyl-β-carboline, is approximately 68 min in blood plasma of the human (Rommelspacher et al.; *Eu J Pharmacol* 2002, 441 (1-2), 115-125), an extension of this value represents a relevant advantage of the inventive compound, in particular at applications for treatment of chronic diseases.

For better evaluation of half times of 9-methyl-β-carboline (9MβC), 6-fluoro-9-methyl-β-carboline (6F9MβC) and 7-fluoro-9-methyl-β-carboline (7F9MβC) in animal organism and more precisely in perilymph (the notified site of action), experiments with guinea pigs were conducted. Therefore, the respective active agent (in total 1.4 mg active agent per ear), packed in 40 µl of a hydrogel (18% Poloxamer 407 and 0.6% alginate), was administered at once in front of the membrane of the round window of narcotized guinea pigs. These membranes separate the air-filled middle ear from the perilymph-filled inner ear. After expiry of the desired time (20 min, 2 h, 8 h or 24 h), each time 5 µL perilymph were removed under anesthesia from the top of the cochlea (apex). Subsequently, the animal was killed. Per each time (20 min, 2 h, 8 h or 24 h) measured values were taken of at least ears and averaged.

The concentration of the corresponding active agent in perilymph samples was determined by high-performance liquid chromatography (HPLC, partly also named as high-pressure liquid chromatography) and measurement of auto fluorescence of the respective active agent. For HPLC the eluent consisted to 45% of 90% acetonitrile and to 55% of ammonium acetate (40 mM, pH<5). The flow rate was 0.4 mL/min and injection volume was 10 µL. Each sample was diluted with 60% methanol, if the signal was too strong. After each run the injection needle was washed with 100% isopropanol. The detection limit was 20 fmol/L.

From the determined active agent concentrations the elimination half times were then calculated. It was shown, that 9-methyl-β-carboline has an elimination half time of approximately 3.4 h, 6-fluoro-9-methyl-β-carboline has an elimination half time of approximately 6.0 h and 7-fluoro-9-methyl-β-carboline has an elimination half time of approximately 5.0 h. By the 1.5-times (7F9MβC) to 1.75-times (6F9MβC) increase of elimination half time of the inventive compounds compared to 9-methyl-β-carboline, a significantly improved bioavailability arises in comparison to the prior art. Overall, it is striking, that the half times determined in the perilymph are higher than the estimated half times in blood (for instance in regard to 9MβC).

Example 4

Quantitative RT-PCR-Experiments I

At neuroblastoma cells it should be examined, to what extent the compounds according to the invention, 6-fluoro-9-methyl-β-carboline and 7-fluoro-9-methyl-β-carboline as well as 9-methyl-β-carboline from prior art, act on expression of important neuroprotective and neurotophic factors, which are known to have a regenerating effect on damaged sensory hair cells. Additionally, they improve the vitality of the nerve cells of the spiral ganglion that mediate the information from the inner ear through the brain stem and further to the auditory center of the brain. In case of a trauma the nervous extensions of the sensory hair cells retract, whereby the signal of the corresponding sound is no more forwarded. The neurotrophic factors cause reconnection between the nervous extensions and the fitting sensory hair cells so that the corresponding sounds can be heard again.

SH-SY5Y cell lines, which were provided by the institute of human genetics of university hospital Eppendorf and which they in turn received from Braunschweig resource center, were used again for the RT-PCR experiments (reverse transcriptase polymerase chain reaction) carried out for this purpose.

The cells were incubated in MEM (Minimum essential medium, Life Technologies) with 10% FCS (fetal calf serum, Biochrom AG) and penicillin/streptomycin (Biochrom AG). The cells were seeded with a density of $1 \times 10^5$ cells/cm$^2$ in 25 cm$^2$ cell culture bottles (Falcon, cell culture treated) with 5 mL medium. Stock solutions of 10 mmol/L of compounds 9-methyl-β-carboline (AC-002 or 9MβC) and 6-fluoro-9-methyl-β-carboline (AC-102 or 6F9MβC), respectively were prepared in distilled water and sterile filtered. One day after the cell seeding the compounds were added in corresponding amounts (5-55 µL) to reach final concentration in the medium of 10 µM, 20 µM and 30 µM for 6F9MβC and 30 μM, 50 μM and 70 μM for 9MβC. The references received only the corresponding amount of solvent (distilled water). The medium was changed once a week.

The cells were regularly microscopically examined and harvest after 2, 7 and 14 days of incubation time, washed with PBS and immediately frozen at −80° C.

The RNA-isolation was done with the HighPure RNA Isolation kit of the company Roche. This isolation includes a DNaseI digestion. The concentration of RNA was measured with nanoDrop spectrometer and the RNA integrity was determined with the aid of the Bioanalyzer 2100 (Agilent). By using random hexamer primers, protector RNA inhibitor (Roche) and transcriptor reverse transcriptase (fermentas), 300 ng RNA were transcribed into cDNA per each sample.

After the reaction, this run was diluted 1:4 and thereof 2 μL per each quantitative RT-PCR were used. This was performed in a LightCycler 480 under standard conditions in the SybrGreen format with annealing temperatures determined for each primer individually. If possible, exon spanning primers were used.

The list of used primers can be found in Table 1.

TABLE 1

Primer sequences for the quantitative RT-PCR experiments. In brackets are listed furthermore the corresponding sequence ID numbers (SEQ-ID). The sequence of all primers is given in 5'-3'-direction.

| target gene | forward primer | reverse primer |
|---|---|---|
| BDNF (brain-derived neurotrophic factor) | GGATGAGGACC AGAAAGT (SEQ-ID 01) | AGCAGAAAGAG AAGAGGAG (SEQ-ID 02) |
| Lif (Leukemia inhibitory factor) | CCAACAACCTG GACAAGCTATG (SEQ-ID 03) | GTGGCGTTGAG CTTGCTGTG (SEQ-ID 04) |
| NT3 (Neurotrophin 3) | CGGAGCATAAG AGTCACC (SEQ-ID 05) | CCTGGCTTCCT TACATCG (SEQ-ID 06) |
| Id2 (Inhibitor of Differentiation 2) | CATCCTGTCCT TGCAGGCTT (SEQ-ID 07) | CCATTCAACTT GTCCTCCTTGT G (SEQ-ID 08) |
| BTG2 (B-cell translocation gene 2) | CAGGAGGCACT CACAGAGCA (SEQ-ID 09) | AATGCGGTAGG ACACCTCATA (SEQ-ID 10) |
| Cbln (Cerebellin 1 precursor Protein) | CAAGTGCCTGG TGGTGT (SEQ-ID 11) | GTTCACTAGTA CCTGGTCGAAG TAG (SEQ-ID 12) |
| DRD2S (short variant of dopamine receptor subtype 2) | GGACTCAATAA CGCAGACCAGA A (SEQ-ID 13) | CGGGCAGCCTC CTTTAGT (SEQ-ID 14) |
| DKK1 (Dickkopf-related protein 1) | CATTGACAACT ACCAGCCGT (SEQ-ID 15) | ATCAGAAGACA CACATATTCCA TT (SEQ-ID 16) |
| Bax | GATGATTGCCG CCGTGGACA (SEQ-ID 17) | CACCTTGGTGC ACAGGGCCTT (SEQ-ID 18) |

TABLE 1-continued

Primer sequences for the quantitative RT-PCR experiments. In brackets are listed furthermore the corresponding sequence ID numbers (SEQ-ID). The sequence of all primers is given in 5'-3'-direction.

| target gene | forward primer | reverse primer |
|---|---|---|
| Bcl2 | GTGTGGAGAGC GTCAACC (SEQ-ID 19) | CTTCAGAGACA GCCAGGAG (SEQ-ID 20) |
| B2M (β2-microglobulin) | ACTGGTCTTTC TATCTCTTGTA CT (SEQ-ID 21) | CTTCAAACCTC CATGATGCT (SEQ-ID 22) |

The specificity was verified by melting curve analysis and subsequent gel electrophoresis. For each PCR the PCR efficiency and the Cq value was determined by the program LinRegPCR and these were used in further calculations. B2M (β2-microglobulin) was identified from multiple reference genes to be suitable for examination conditions. All results are results relative to the corresponding reference conditions, at which only solvent was administered for the specified period of time (i.e. 2 days, 7 days or 14 days). In FIGS. 5A to 5I are also relative gene expressions (relative to reference conditions) presented. Here, the 2-day exposition is presented in light grey, the 7-day exposition in dark grey and the 14-day exposition in black. Every measured value from FIGS. 5A-5I represents a mean value of 3 independent biologic samples.

Figure 5A:
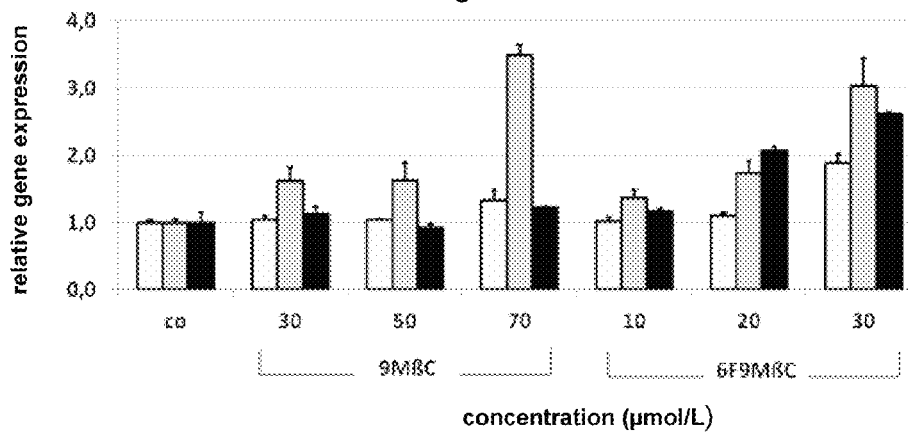
FIG. 5 shows relative gene expression of BDNF (brain-derived neurotrophic factor, FIG. 5A), of Lif (Leukemia inhibitory factor, FIG. 5B), of NT3 (Neurotrophin 3, FIG. 5C), of Id2 (Inhibitor of Differentiation 2, FIG. 5D), of BTG2 (B-cell translocation gene 2, FIG. 5E), of Cbln (Cerebellin 1 precursor protein, FIG. 5F), of DRD2S (short variant of dopamine receptor subtype 2, FIG. 5H), of DKK1 (Dickkopf-related protein 1, FIG. 5I) as well as quotient Bax/Bcl2 (FIG. 5G) each after 2 days (light grey bar), 7 days (dark grey bar) and 14 days (black bar) exposure of SH-SY5Y cells towards 6F9MβC (10 μM, 20 μM & 30 μM) or 9MβC (30 μM, 50 μM & 70 μM). Relative gene expression means gene expression of respective factor relative to the reference conditions.

FIG. 5A shows the relative gene expression of neurotrophin BDNF (brain-derived neurotrophic factor) after 2 days, 7 days and 14 days exposition towards 6F9MβC (10 μM, 20 μM & 30 μM) or 9MβC (30 μM, 50 μM & 70 μM). When comparing the BDNF expression after exposition with 30 μM 6F9MβC or 9MβC, already at this concentration it is shown, that the expression induced by 6F9MβC is approximately twice as high as the expression induced by 9MβC.

Figure 5B:
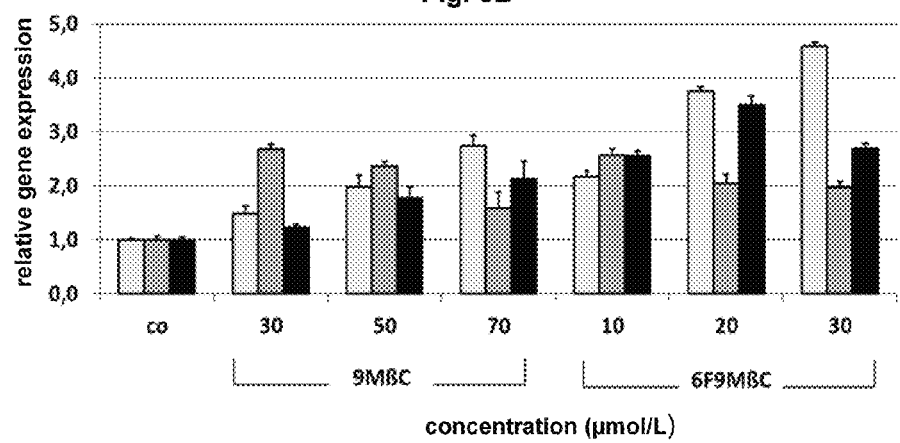

FIG. 5B shows the relative gene expression of Lif (Leukemia inhibitory factor), which stimulates cell differentiation and inhibits proliferation, after 2 days, 7 days and 14 days exposition towards 6F9MβC (10 μM, 20 μM & 30 μM) or 9MβC (30 μM, 50 μM & 70 μM). When comparing the Lif expression after exposition with 30 μM 6F9MβC or 9MβC, already at this concentration it is shown, that the expression of Lif induced by 6F9MβC after 2-day exposition is approximately three times as high as the expression induced by 9MβC. Also after 14-day exposition towards 6F9MβC the Lif expression is approximately twice as high compared to 9MβC. Only after 7-day exposition towards 6F9MβC the expression of Lif seems to be slightly lower compared to 9MβC. The high expression at low concentrations of 6F9MβC is also remarkable.

Figure 5C:
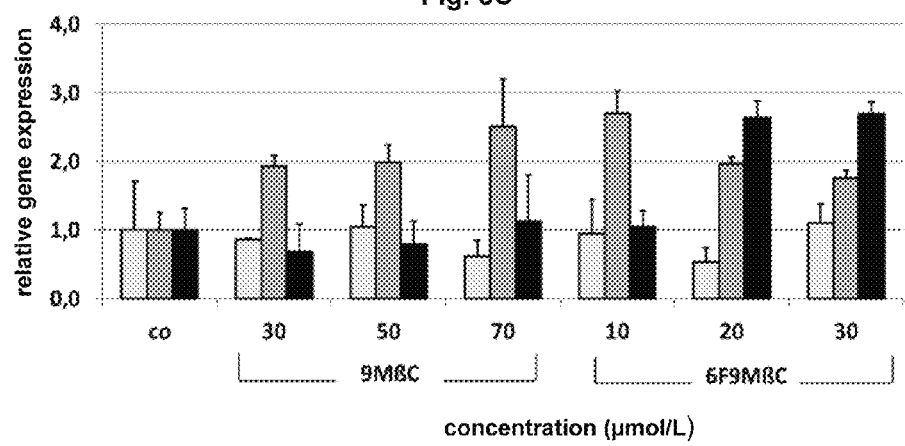

FIG. 5C shows the relative gene expression of neurotrophin NT3 (neurotrophin 3) after 2 days, 7 days and 14 days exposition towards 6F9MβC (10 μM, 20 μM & 30 μM) or 9MβC (30 μM, 50 μM & 70 μM). When comparing the NT3 expression after exposition with 30 μM 6F9MβC or 9MβC, already at this concentration it is shown, that the expression of NT3 by 6F9MβC after 14-day exposition is approximately 3.5-times higher than the expression induced by 9MβC. The high expression at low concentrations of 6F9MβC, especially after 7-day exposition with only 10 μM 6F9MβC is also remarkable.

Figure 5D:
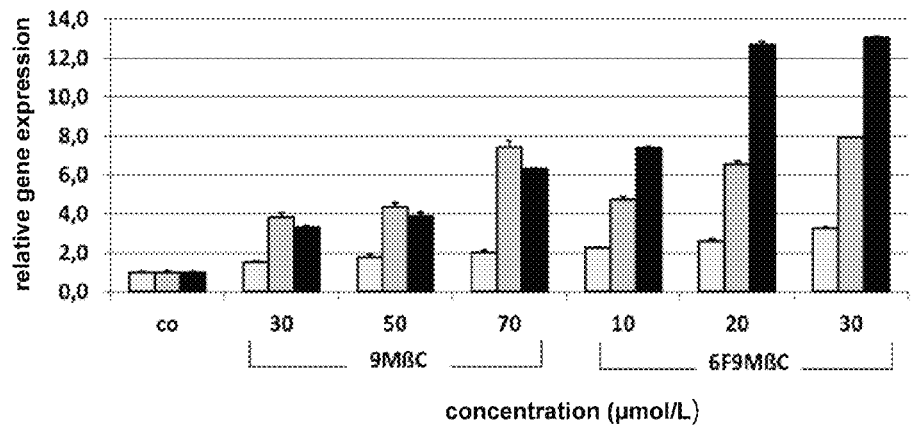

FIG. 5D shows the relative gene expression of Id2 (inhibitor of differentiation 2), which inhibits cell differentiation and thus promotes proliferation. It was also described, that mice, at which the gene was deactivated, show neurodegenerative phenomena. The relative gene expression of Id2 after 2 days, 7 days and 14 days exposition towards 6F9MβC (10 μM, 20 μM & 30 μM) or 9MβC (30 μM, 50 μM & 70 μM) is shown. When comparing the Id3 expression after exposition with 30 μM 6F9MβC or 9MβC, already at this concentration it is shown, that the expression of Id2 induced by 6F9MβC is approximately 2-times to 3.5-times higher than the expression induced by 9MβC. The high expression of Id2 at low concentrations of 6F9MβC is here also remarkable.

Figure 5E:
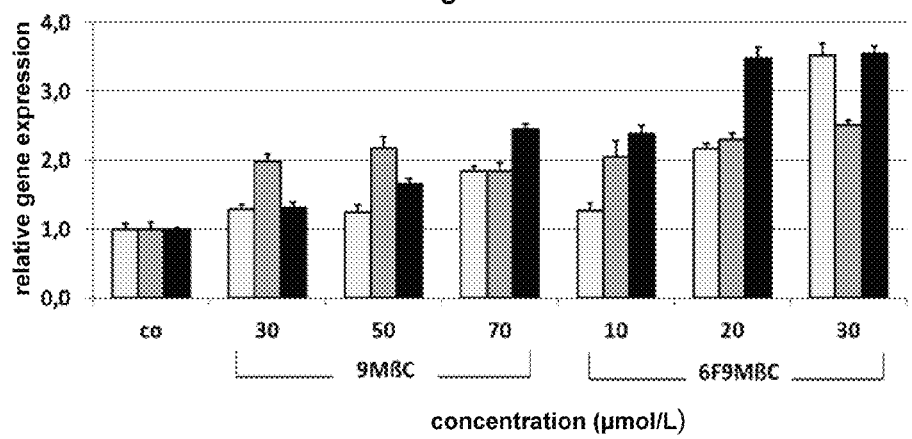
Figure 5:
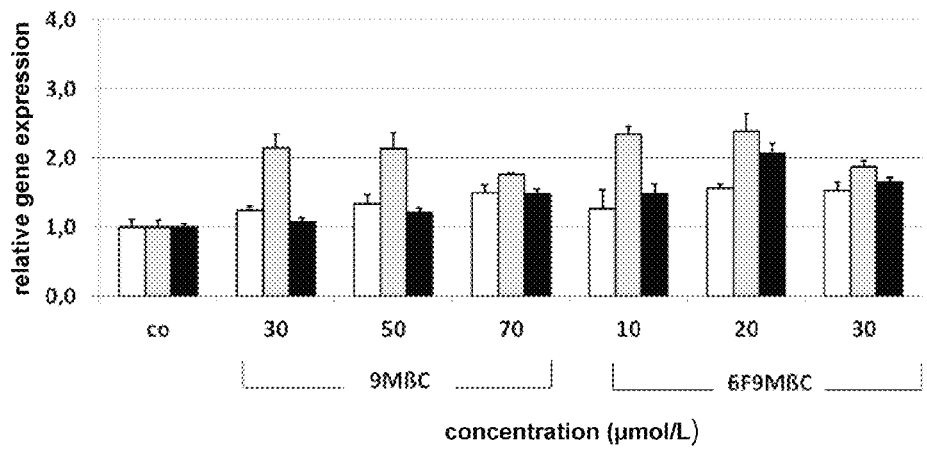

FIG. 5E shows the relative gene expression of neuroprotector BTG2 (B-cell translocation gene 2) after 2 days, 7 days and 14 days exposition towards 6F9MβC (10 μM, 20 μM & 30 μM) or 9MβC (30 μM, 50 μM & 70 μM). When comparing the BTG2 expression after exposition with 30 μM 6F9MβC or 9MβC, already at this concentration it is shown, that the expression of BTG2 induced by 6F9MβC is approximately 1.25-times to 2.7-times higher than the expression induced by 9MβC. It is also remarkable, that already at 10 μM 6F9MβC an expression of BTG2 comparable to the highest concentration of 9MβC is observed (except after 2-day exposition).

FIG. 5F shows the relative gene expression of neuroprotector Cbln (cerebellin 1 precursor protein) after 2 days, 7 days and 14 days exposition towards 6F9MβC (10 μM, 20 μM & 30 μM) or 9MβC (30 μM, 50 μM & 70 μM). When comparing the Cbln expression after exposition with 30 μM 6F9MβC or 9MβC, already at this concentration it is shown, that the expression of Cbln induced by 6F9MβC is approximately 1.5-times higher than the expression induced by 9MβC (except after 2-day exposition). Only at 20 μM 6F9MβC the expression of Cbln seems to be even higher.

Figure 5G:
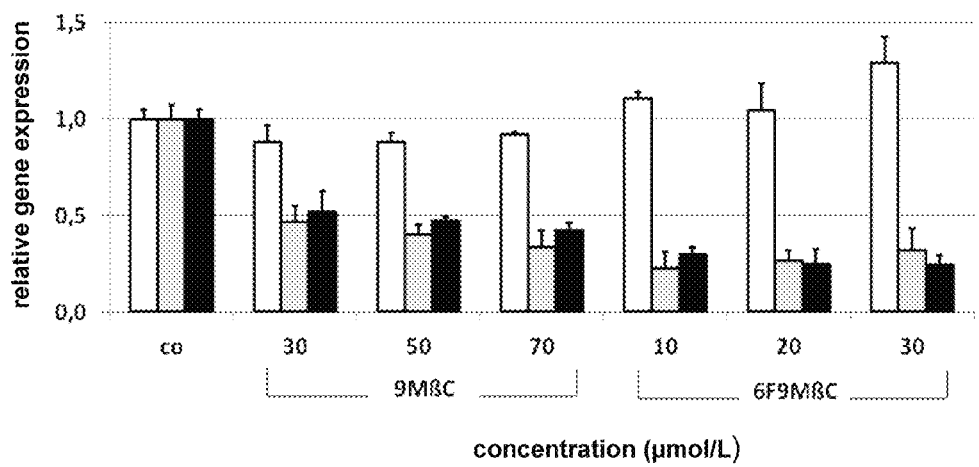

FIG. 5G shows the quotient of gene expression of Bac and Bcl2, which is regarded as apoptosis marker, after 2 days, 7 days and 14 days exposition towards 6F9MβC (10 μM, 20 μM & 30 μM) oder 9MβC (30 μM, 50 μM & 70 μM). The smaller the quotient Bax/Bcl2, the lower the apoptosis. When comparing the quotient Bax/Bcl2 after exposition with 30 μM 6F9MβC or 9MβC, it is significantly lower after 6F9MβC than after 9MβC (except after 2-day exposition). The low quotient Bax/Bcl2 at low concentrations of 6F9MβC is also remarkable.

Figure 5H:
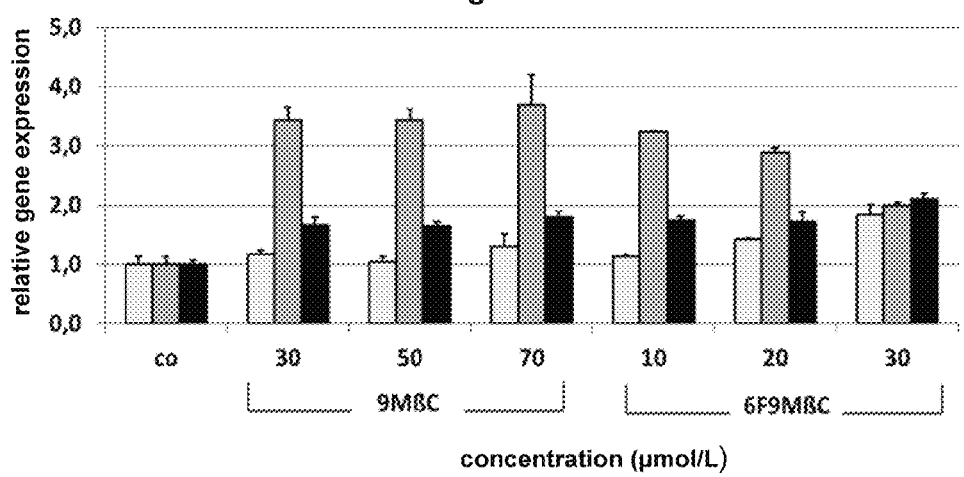

FIG. 5H shows the quotient of gene expression of DRD2S (short variant of dopamine receptor subtype 2) after 2 days, 7 days and 14 days exposition towards 6F9MβC (10 μM, 20 μM & 30 μM) oder 9MβC (30 μM, 50 μM & 70 μM). When comparing DRD2S expression after exposition with 30 μM 6F9MβC or 9MβC, at this concentration it is shown, that the expression of DRD2S induced by 6F9MβC after 2-day and 14-day exposition is higher than the expression induced by 9MβC and after 7-day exposition it is lower than the expression induced by 9MβC. At low concentrations of 6F9MβC the expression of DRD2S after 7-day expression seems to be comparable with the expression induced by 9MβC.

Figure 5I:
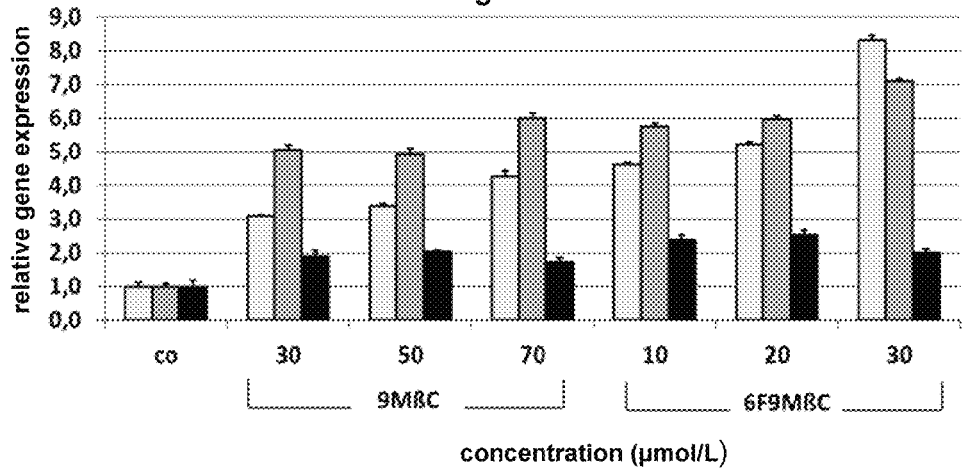

FIG. 5I shows the relative gene expression of factor DKK1 (Dickkopf-related protein 1) that is of significance for differentiation of nerve cells and that after current insights plays a role at traumas of sensory cells, after 2 days, 7 days and 14 days exposition towards 6F9MβC (10 μM, 20 μM & 30 μM) oder 9MβC (30 μM, 50 μM & 70 μM). When comparing DKK1 expression after exposition with 30 μM 6F9MβC or 9MβC, particularly at shorter expositions (2 days and 7 days) it is shown, that the expression of DKK1 induced by 6F9MβC is 1.4-times to 2.7-times higher than the expression induced by 9MβC. For 14-day exposition the values are comparable. and after 7-day exposition it is lower than the expression induced by 9MβC. It is also remarkable, that already at 10 μM 6F9MβC a comparable or even higher expression of DKK1 is noticed compared to the expression at the highest concentration of 9MβC.

Overall, it is shown, that the inventive 6-fluoro-9-methyl-β-carboline has a beneficial effect on nearly all examined cellular factors, which have directly or indirectly influence on the differentiation and proliferation of cells and thus also on regeneration of sensory tissues after traumas, compared to 9-methyl-β-carboline from the state of the art. Especially emphasized are the factors BDNF and Lif that belong to the most important factors for cellular repair processes after traumas in the inner ear. Therefore, 6-fluoro-9-methyl-β-carboline according to the invention has the potential not only to be applied successfully in treatment of diseases and/or damages of the inner ear, but also in lower concentrations as the methyl-β-carbolines from the state of the art.

Example 5

Quantitative RT-PCR Experiments II

Analogous to example 4 RT-PCR experiments with the inventive active agent 7-fluoro-9-methyl-β-carboline (7F9MβC) were also performed for some important cellular factors. The experimental procedure was here identical to the experiments with 6-fluoro-9-methyl-β-carboline and 9-methyl-β-carboline. Here the same (like for 6F9MβC) final concentrations of 30 μM, 50 μM and 70 μM 7F9MβC for the culture medium were employed. The examined factors were BDNF (brain-derived neurotrophic factor), Lif (Leukemia inhibitory factor), DRD2S (short variant of dopamine receptor subtype 2) as well as DKK1 (Dickkopf-related protein 1). The same primers, that were already listed for the respective target genes in example 4 (Tab. 1) were used. As already noted, especially BDNF and Lif belongs to the most important factors for cellurar repair processes after traumas in the inner ear.

Figure 6A:
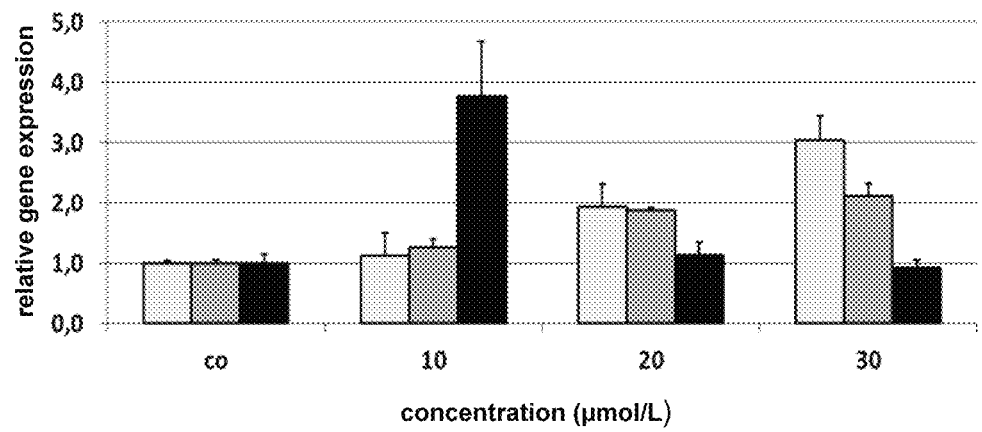
FIG. 6 shows relative gene expression of BDNF (brain-derived neurotrophic factor, FIG. 6A), of Lif (Leukemia inhibitory factor, FIG. 6B), of DRD2S (short variant of dopamine receptor subtype 2, FIG. 6C) and of DKK1 (Dickkopf-related protein 1, FIG. 6D) each after 2 days (light grey bar), 7 days (dark grey bar) and 14 days (black bar) exposure of SH-SY5Y cells towards 7F9MβC. Relative gene expression means gene expression of respective factor relative to the reference conditions.

FIG. 6A shows the relative gene expression of neurotrophin BDNF (brain-derived neurotrophic factor) after 2 days, 7 days and 14 days exposition towards 7F9MβC (10 μM, 20 μM & 30 μM). When comparing the BDNF expression after exposition with 30 μM 7F9MβC or 9MβC (FIG. 5A), it is shown for a 2-day exposition, that the BDNF expression induced by 7F9MβC is approximately three times higher than the expression induced by 9MβC. For longer expositions the values are comparable.

Figure 6B:
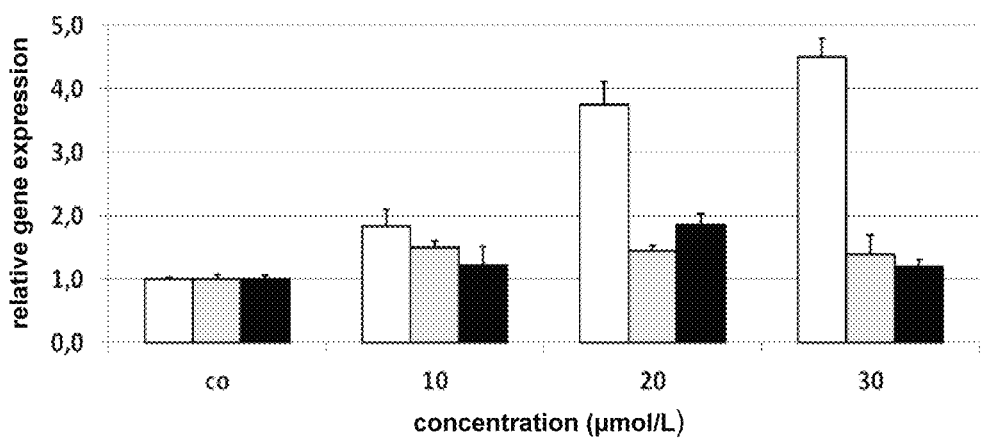

FIG. 6B shows the relative gene expression of Lif (Leukemia inhibitory factor), which stimulates cell differentiation and inhibits proliferation, after 2 days, 7 days and 14 days exposition towards 7F9MβC (10 μM, 20 μM & 30 μM). When comparing the Lif expression after exposition with 30 μM 7F9MβC and with 30 μM 9MβC (FIG. 5B), it is shown at 2-day exposition, that the expression of Lif induced by 7F9MβC is approximately three times higher than the expression induced by 9MβC. At 7-day exposition the induction by 7F9MβC is weaker and at 14-day exposition the values are comparable. The high expression of Lif after 2-day exposition with 20 μM 7F9MβC is also remarkable.

Figure 6C:
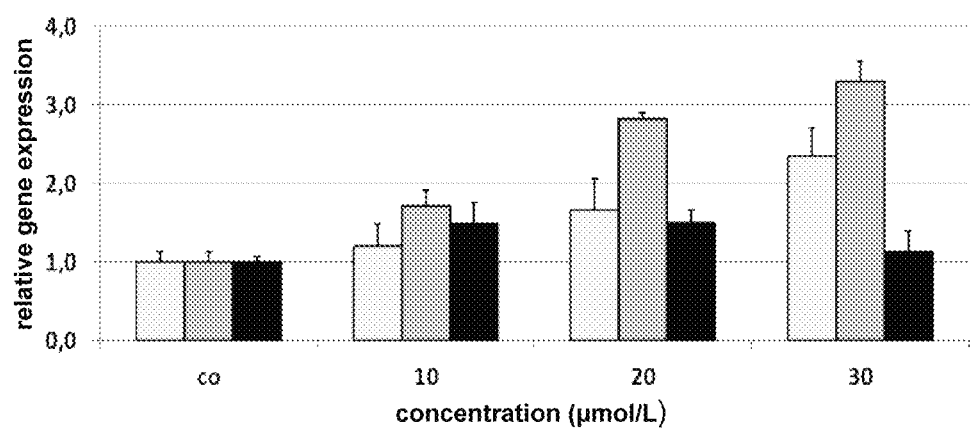

FIG. 6C shows the relative gene expression of DRD2S (short variant of dopamine receptor subtype 2) after 2 days, 7 days and 14 days exposition towards 7F9MβC (10 μM, 20 μM & 30 μM). When comparing DRD2S expression after exposition with 30 μM 7F9MβC and with 30 μM 9MβC (FIG. 5H), it is shown for a 2-day exposition, that the expression of DRD2S induced by 7F9MβC is twice as high as the expression induced by 9MβC. After 7-day exposition the values are comparable and after 14-day exposition the induction by 7F9MβC is slightly weaker than the induction by 9MβC.

Figure 6D:
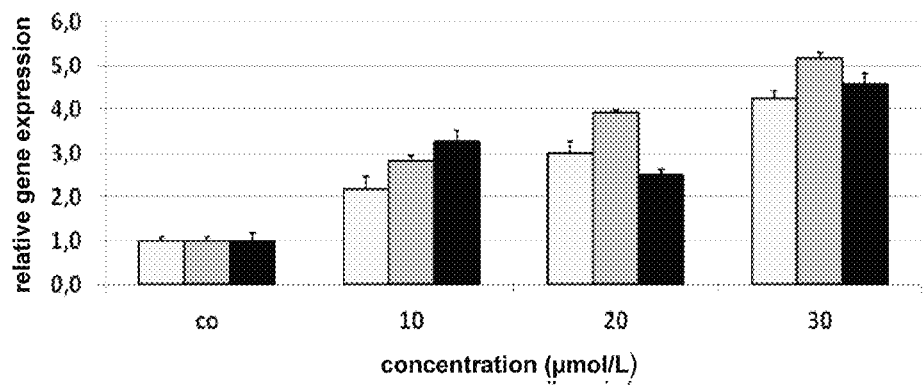

FIG. 6D shows the relative gene expression of factor DKK1 (Dickkopf-related protein 1) that is of significance for differentiation of nerve cells and that after current insights plays a role at traumas of sensory cells, after 2 days, 7 days and 14 days exposition towards 7F9MβC (10 μM, 20 μM & 30 μM). When comparing DKK1 expression after exposition with 30 μM 7F9MβC and with 30 μM 9MβC (FIG. 5I), it is shown for 2-day exposition, that the expression of DKK1 induced by 7F9MβC is 1.4-times higher than the expression induced by 9MβC. After 7-day exposition the values are comparable and after 14-day exposition the induction by 7F9MβC is 2.2-times higher than the induction by 9MβC.

Overall, it is noted, that 7-fluoro-9-methyl-β-carboline in comparison to 9-methyl-β-carboline from the state of the art achieves particularly higher effects at short expositions. One possible explanation is, that 7-fluoro-9-methyl-β-carboline is more lipophilic than 9-methyl-β-carboline and by that penetrates cells faster and thus reaches in the cell higher concentrations faster. From a therapeutically point of view such advantages are desirable, because they enable an efficient and shorter treatment duration, which serves the benefit of the patient. From a therapeutically position, 7-fluoro-9-methyl-β-carboline is therefore superior to 9-methyl-β-carboline from the state of the art in treatment of acute damages of the inner ear like for instance acoustic trauma and hearing loss.

Example 6

Immunohistochemical Experiments

In the following, it should be investigated on a histological base, how the administration of 9-methyl-β-carboline (9MβC) or of 6-fluoro-9-methyl-β-carboline (6F9MβC) to guinea pigs affects the acoustic trauma-induced dying of outer hair cells (OHC) in the inner ear. At this point it shall be noted, that the inner hair cells (IHC) are more insensitive to any trauma.

To induce an acoustic trauma, guinea pigs were anesthetized with 60 mg/kg ketamine and 8 mg/kg xylazine. Then Bepanten ointment (Bayer) was administered to the eyes and the animal was put in a soundproof chamber. A calibrated speaker was placed directly above the head of the animal, wherein it was set to emit a half octave band, centered around 8 kHz, with a volume of 110 dB for duration of 30 minutes.

The 6-fluoro-9-methyl-β-carboline and 9-methyl-β-carboline, respectively, packed in a hydrogel (18% Poloxamer 407 and 0.6% alginate), was for every experiment freshly prepared and stored until application in the fridge at +4° C.

The thermosensitive, liquid mixture was administered under view by a Hamilton syringe directly in front of the round window membrane of the middle ear (10 μL). The first dose 6-fluoro-9-methyl-β-carboline (e.g. 0.07 mg) was administered one hour after the acoustic trauma in a concentration of 0.007 mg/μL and the second dose 6-fluoro-9-methyl-β-carboline (0.035 mg in a volume of 5 μL) on day 3. Here, only one ear per animal was treated, while the second ear served as intra-individual control. The control here is particularly abbreviated to "contr.". In comparative experiments it was found, that administration of just an active agent vehicle (hydrogel) has no effect in comparison to a fully untreated ear. For each active agent (including the controls) four guinea pigs were examined.

Figure 7:
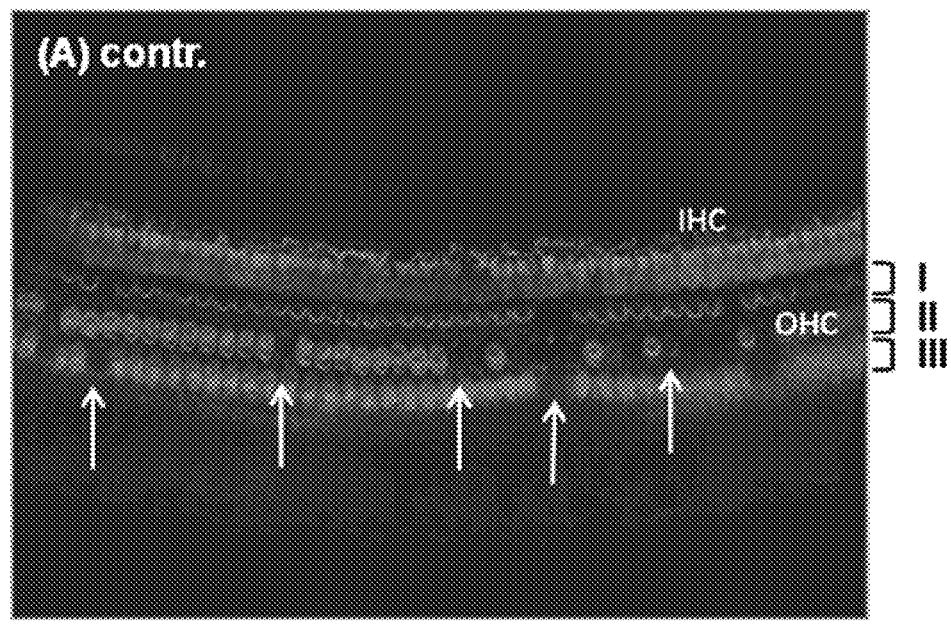
FIG. 7: Fluorescence microscopic image of cochlea cuts after immunohistochemical staining with phalloidin (marked with Alexa Fluor® 488) of a guinea pig after acoustic trauma, wherein one ear was treated with 6-fluoro-9-methyl-β-carboline (6F9MβC, total 0.105 mg per ear) (FIG. 7B) and the second untreated ear served as intra-individual control (also named as "contr.", FIG. 7A). Inner hair cells (IHC) and the three rows (I, II, III) outer hair cells (OHC) can be recognized. Dead cells are highlighted with white arrows and demonstrate the damaging effect of the acoustic trauma. Scale=25 μm.
Figure 8:
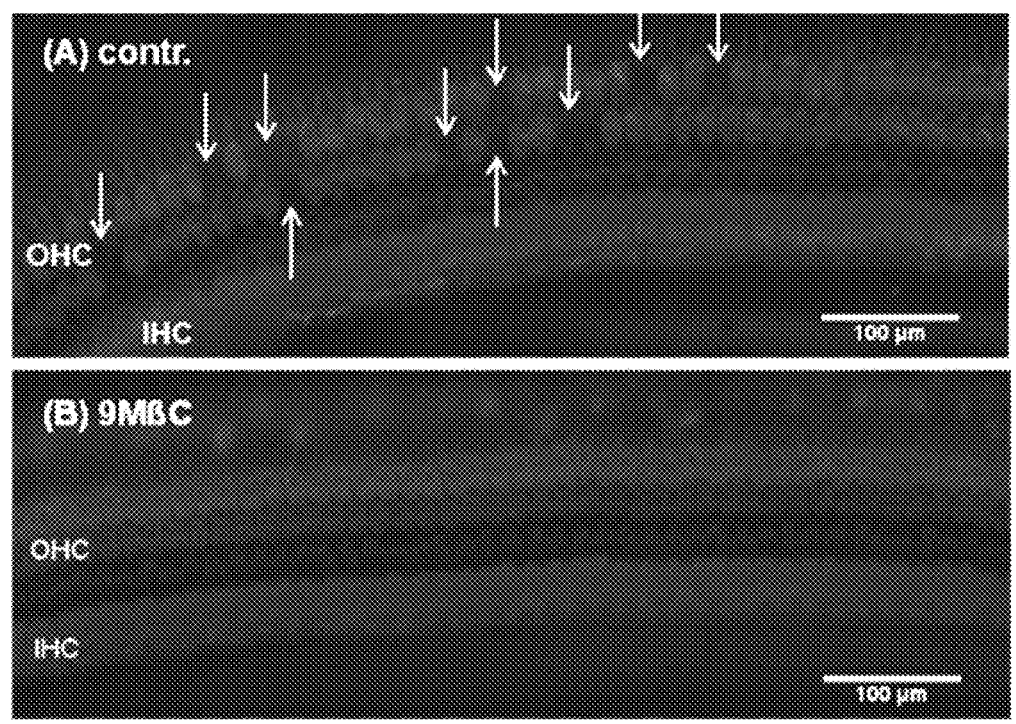
FIG. 8: Fluorescence microscopic image of cochlea cuts after immunohistochemical staining with phalloidin (marked with Alexa Fluor® 488) of a guinea pig after acoustic trauma, wherein one ear was treated with 9-methyl-β-carboline (9MβC, in total 0.2 mg per ear) (FIG. 8B) and the second untreated ear served as intra-individual control (also named as "contr.", FIG. 8A). Inner hair cells (IHC) and outer hair cells (OHC) can be recognized. Dead cells are highlighted with white arrows and demonstrate the damaging effect of the acoustic trauma. Scale=100 μm.

On day 14 after the acoustic trauma the region of the ear was dissected so that it contained the cochlea. The preparation was put into ice cold 4% paraformaldehyde (PFA) for 24 hours and stored at +4° C. After PFA-fixation the preparation was rinsed twice with a phosphate-buffered sodium chloride solution (PBS) and afterwards placed for decalcification in a 10% ethylenediaminetetraacetic acid (EDTA). After at least 48 hours the preparation was rinsed twice with PBS and afterwards the cochlea was dissected out. The whole organ of corti that contains the sensory cells was then dissected out of the cochlea and cut into four segments of equal length. Every segment corresponds to the organ of corti of ¾ cochlea turn. In this way the sound induced damage can be localized and quantified. The cuts were placed for 10 minutes in PBS, which contained 2% bovine serumalbumine (BSA) and (mit Alexa Fluor® 488-labelled phalloidin (Invitrogen, catalogue #A12379) in a dilution of 1:40. Afterwards the cuts were washed for 10 minutes with PBS three times and placed flatly on a slide. A drop Pro Long DAPI, which contained fixing medium (Invitrogen, cat # P36935), was added on the cuts, which then were covered by a coverslip. The preparation was subsequently sealed by nail polish. Images of the cuts in 40-times magnification were taken by a fluorescence microscope (Keyence). The FIGS. 7 and 8 show representative results of examinations on each four guinea pigs.

Figure 7B:
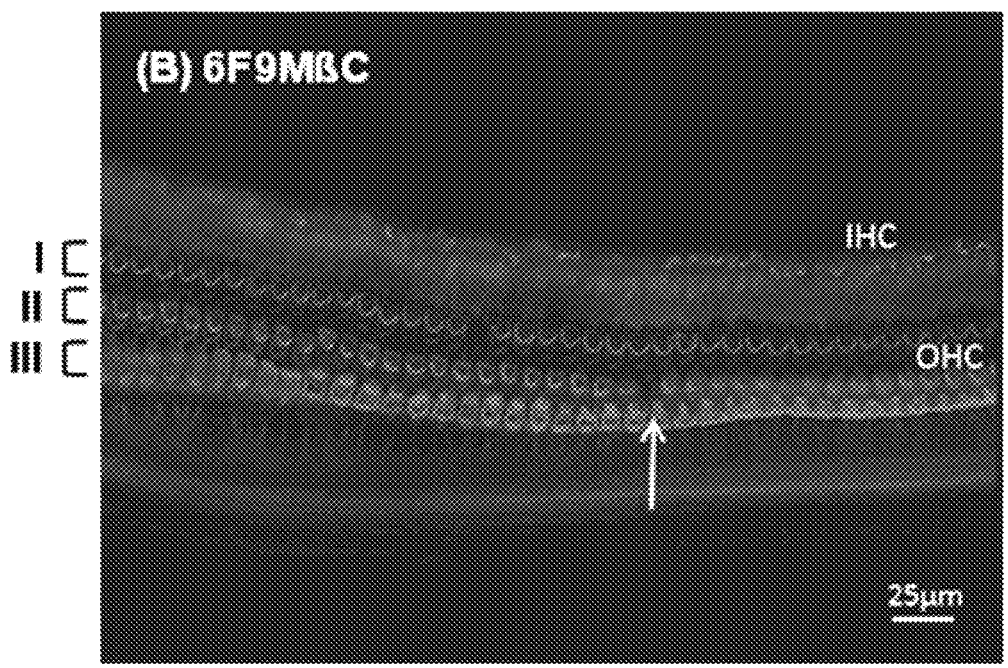

It was shown in the untreated controls (see FIG. 7a and FIG. 8A), that the acoustic trauma led to a strong dying of outer hair cells. This dying could be prevented by a single intratympanic administration of only a total 0.105 mg 6-fluoro-9-methyl-β-carboline (see FIG. 7B). Also the administration of 9-methyl-β-carboline could counteract the dying of outer hair cells (see FIG. 8B), wherein a significantly increased dose (0.2 mg 9-methyl-β-carboline) is needed compared to the inventive 6-fluoro-9-methyl-β-carboline. Therefore, the inventive 6-fluoro-9-methyl-β-carboline is not only suitable for treatment of hearing damages, but it is also more efficient than 9-methyl-β-carboline from the state of the art.

Example 7

Acoustically Evoked Potentials

In the following the effect of 6-fluoro-9-methyl-β-carboline (6F9MβC) as well as 9-methyl-β-carboline (9MβC) on the change of the hearing threshold induced by an acoustic trauma should be investigated on a guinea pig model.

To trigger an acoustic trauma, guinea pigs were anesthetized with 60 mg/kg ketamine and 8 mg/kg xylazine. Then Bepanten ointment (Bayer) was administered to the eyes and the animal was put in a soundproof chamber. A calibrated speaker was placed directly above the head of the animal, wherein it was set to emit a half octave band, centered around 8 kHz, with a volume of 110 dB for duration of 30 minutes.

As measure for evaluation of the hearing threshold of the guinea pig acoustically evoked potentials were measured. Therefore, the electrophysiological activity of the nerve cells in the brain stem that forward impulses from the inner ear was derived after sonication of the ear with 8, 11.3, 16, 22.6 and 32 kHz. The sonification was carried out ascendingly from 0 dB to 90 dB in single steps of 5 dB.

The measurement was carried out 3 days before the acoustic trauma (D-3), 30 minutes after the acoustic trauma (D0) as well as 14 days after the acoustic trauma (D14).

Per animal one ear was not treated and used as intra-individual control (hierin partly abbreviated to "contr.") and the second ear was treated with 6-fluoro-9-methyl-β-carboline. Therefore, one hour after the acoustic trauma a dose of 0.12 mg 6-fluoro-9-methyl-β-carboline (in a hydrogel as vehicle) was administered intratympanically. 3 days after the acoustic trauma a further intratympanic administration of 0.06 mg 6-fluoro-9-methyl-β-carboline was carried out. The measurements were conducted on four guinea pigs (n=4).

In comparative experiments it was found, that administration of just an active agent vehicle (hydrogel) has no effect in comparison to a fully untreated ear.

Afterwards, the remaining shift of hearing threshold (also named as permanent shift of hearing threshold) was determined from the measured values before the acoustic trauma (D-3) and after 14 days (D14). From the measured values directly after the acoustic trauma (D0) and after 14 days (D14) the recovery from the trauma (D0-D14) was also determined.

Figure 9:
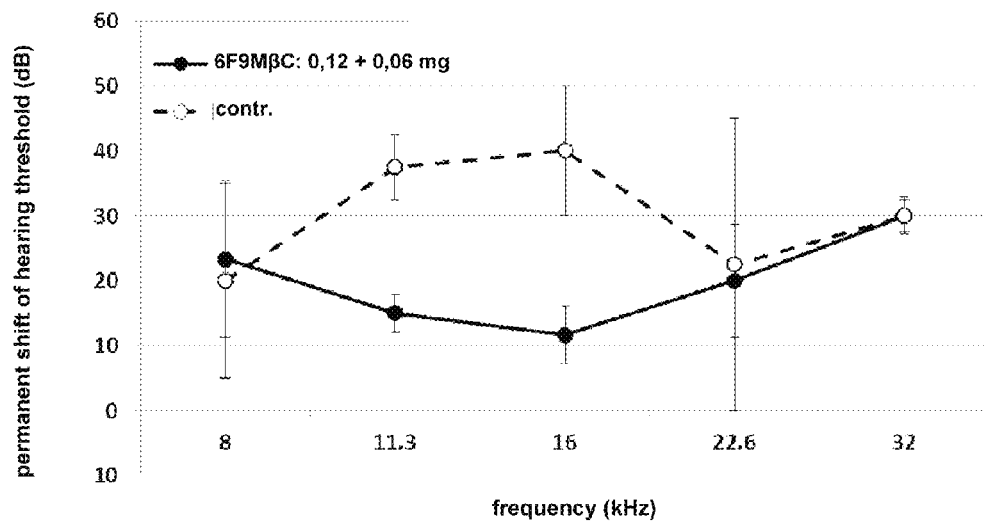
FIG. 9 shows the permanent shift of hearing threshold of guinea pig after an acoustically induced noise trauma, wherein one ear after the noise trauma was treated with 6-fluoro-9-methyl-β-carboline (6F9MβC, in total 0.18 mg per ear) and the second untreated ear served as intra-individual control (contr.). The hearing threshold was determined by measuring acoustically evoked brainstem potentials, which were measured 3 days before the acoustic noise trauma (D-3), 30 minutes after the acoustic noise trauma (D0) as well as 14 days after the acoustic noise trauma (D14). The permanent shift of hearing threshold is calculated from the measured values D14-D-3. The shown values are mean values from four independent measurements (n=4).

It was shown, that regarding to the after 14 days still remaining hearing impairment (see FIG. 9), the administration of 6-fluoro-9-methyl-β-carboline (total 0.18 mg) led to a significant reduction of the hearing threshold in comparison to the untreated control. Especially at a sound frequency of 11.3 and 16 kHz, respectively, a reduction of the hearing threshold of approximately 20 dB or 30 dB was shown by the inventive 6-fluoro-9-methyl-β-carboline.

Figure 10:
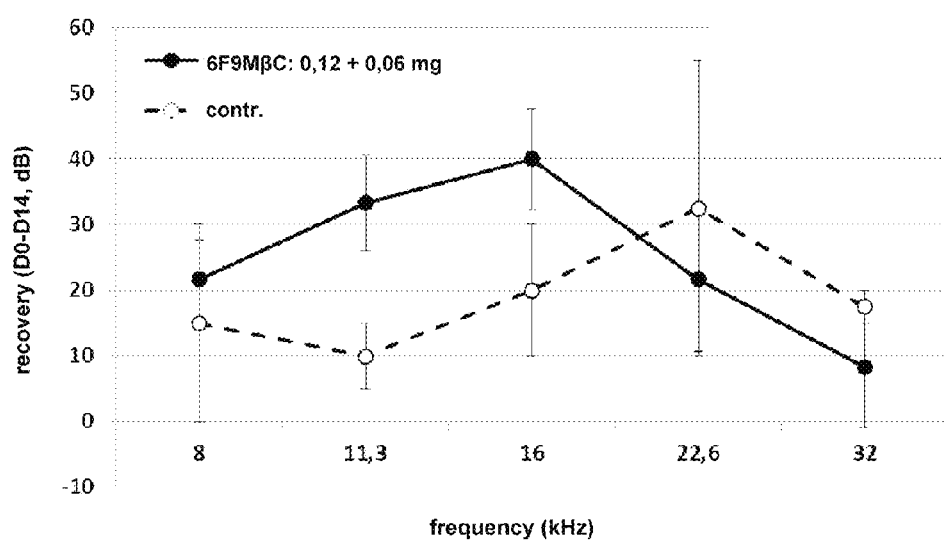
FIG. 10: Like FIG. 9, wherein however the recovery of the hearing threshold of a guinea pig after an acoustically induced noise trauma is shown. This is calculated from the measured values D0-D14. The shown values are mean values from four independent measurements (n=4).

Also regarding to the recovery from the acoustic trauma (see FIG. 10) the recovery compared to the untreated control could be significantly improved by administration of 6-fluoro-9-methyl-β-carboline (total 0.18 mg). So, at sound frequencies of 8, 11.3 and 16 kHz, respectively a by approximately 5 dB, 25 dB or 20 dB improved recovery due to the inventive 6-fluoro-9-methyl-β-carboline was shown in comparison to the untreated ear.

Analogous to the above performed experiments with 6-fluoro-9-methyl-β-carboline, also corresponding experiments with 9-methyl-β-carboline were performed. The experimental procedure was nearly identical, wherein of course 9-methyl-β-carboline instead of 6-fluoro-9-methyl-β-carboline was used. The total dose of 9-methyl-β-carboline was here 0.2 mg and 0.35 mg per ear, respectively.

Figure 11:
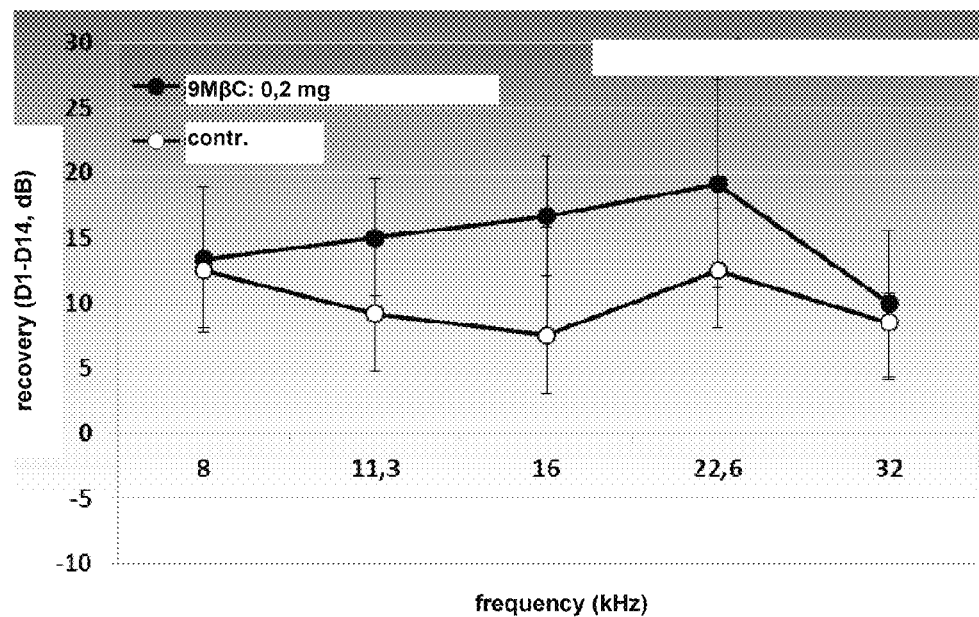
FIG. 11 shows the recovery of the hearing threshold of a guinea pig after an acoustically induced noise trauma, wherein one ear after the noise trauma was treated with 9-methyl-β-carboline (9MβC, in total 0.2 mg per ear) and the second untreated ear served as intra-individual control (contr.). The hearing threshold was determined by measuring acoustically evoked brainstem potentials, which were measured 3 days before the acoustic noise trauma (D-3), after the acoustic noise trauma (D1) as well as 14 days after the acoustic noise trauma (D14). The recovery of the hearing threshold is calculated from the measured values D1-D14.
Figure 12:
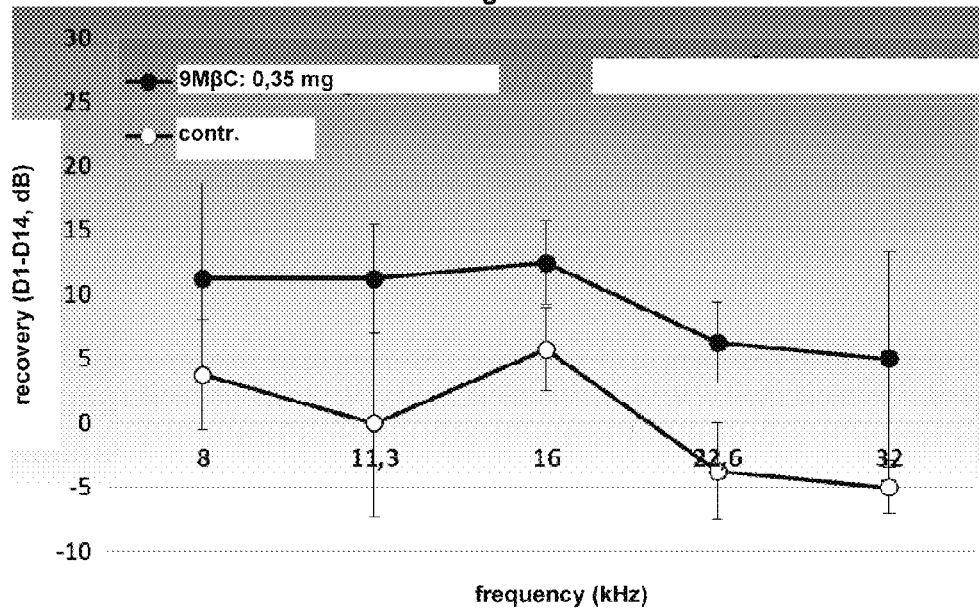
FIG. 12: Like FIG. 11, wherein however 0.35 mg of 9-methyl-β-carboline were administered per ear.

The 9-methyl-β-carboline from the state of the art also promoted demonstrably the recovery in comparison to the untreated control (see FIGS. 11 and 12). In comparison to 6-fluoro-9-methyl-β-carboline, only an improvement of the recovery by approximately 5 dB to maximal 10 dB was shown when the dose was slightly increased by 0.2 mg (see FIG. 11). Also a further increased dose of 0.35 mg 9-methyl-β-carboline (twice as high as 6-fluoro-9-methyl-β-carboline) showed only an improvement of about 10 dB (see FIG. 12).

Example 8

Degradation in the Lever to Toxic Degradation Products

In the following, it should be investigated, if the inventive 6-fluoro-9-methyl-β-carboline (6F9MβC) is metabolized in the liver to known toxic degradation products.

For β-carbolines it is long known, that these are transformed to methylated β-carbolinium cations by a N-methyltransferase catalyzes reaction. These have some toxicological properties in common with 1-methyl-4-phenylpyridinium (MPP+, also known as Parkinson neurotoxin), because they can among others inhibit the mitochondrial respiration and have a neurotoxic effect. Especially toxic are dimethylated β-carbolinium cations, i.e. the 2,9-dimethyl-β-carbolinium cations. These are formed by sequential methylation at position 2 and 9. Thus, in the following, it should be investigated, if the inventive 6-fluoro-9-methyl-β-carboline (6F9MβC) is metabolized in the liver to the corresponding toxins 6-fluoro-2,9-dimethyl-β-carbolinium cation (directly derived from 6F9MβC) and 2,9-dimethyl-β-carbolinium cation (derived from 9MβC), respectively.

To identify these substances by HPLC, 6-fluoro-2,9-dimethyl-β-carbolinium cation (6F29DMβC) as well as 2,9-dimethyl-β-carbolinium cation (29DMβC) were synthesized on-site the respective retention times determined by reference HPLC measurements. Also a reference measurement with pure 6-fluoro-9-methyl-β-carboline (6F9MβC) was performed.

To simulate the degradation process in the liver, different concentrations (1 µM, 10 µM and 100 µM) of 6-fluoro-9-methyl-β-carboline (6F9MβC) were incubated with homogenized rat liver for an hour under physiological conditions (37° C. in physiological phosphate-buffered sodium chloride solution, PBS). Subsequently, a HPLC measurement of the filtrated extract was carried out.

The characterization of each substance was achieved by high-performance liquid chromatography (HPLC, partly also named as high-pressure liquid chromatography). For HPLC the eluent consisted to 45% of 90% acetonitrile and to 55% of ammonium acetate (40 mM, pH<5). The flow rate was 0.4 mL/min and injection volume was 10 µL. Each sample was diluted with 60% methanol, if the signal was too strong. For instance the sample from the liver homogenate had to be diluted by 1:40 before the measurement to be in the dynamic range of the analytical method.

Figure 13A:
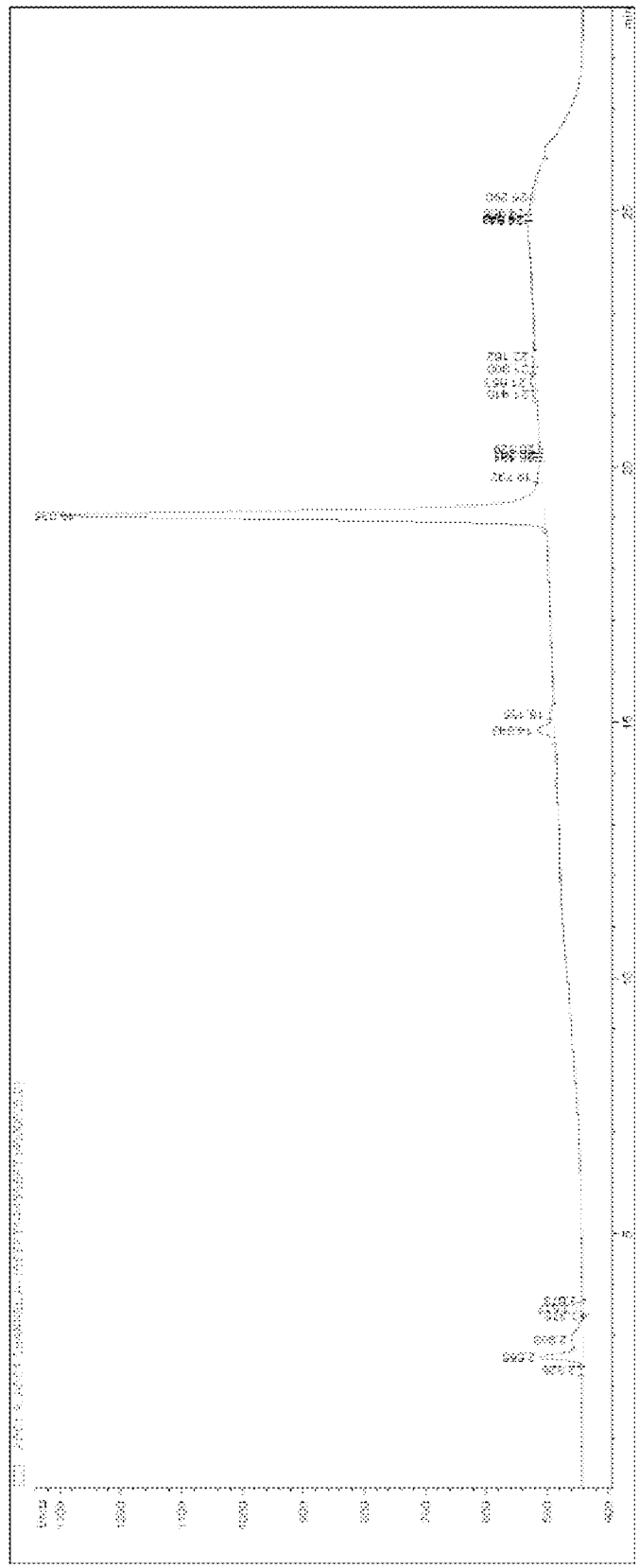
FIG. 13: HPLC chromatograms of untreated 6-fluoro-9-methyl-β-carboline (6F9MβC, FIG. 13A), 6-fluoro-9-methyl-β-carboline incubated with liver homogenate for 1 h (FIG. 13B), 6-fluoro-2,9-dimethyl-β-carboliniumion (6F29DMβC, FIG. 13C) and 2,9-dimethyl-β-carboliniumion (29DMβC, FIG. 13D). The retention times were 19.0 min (6F9MβC & liver+6F9MβC), 10.1 min (6F29DMβC) and 9.1 min (29DMβC). Column: Phenomenex Luna 3uC18 (2) 100A; eluent: ACN90%/NH$_4$Ac 40 mM [45/55]
Figure 13B:
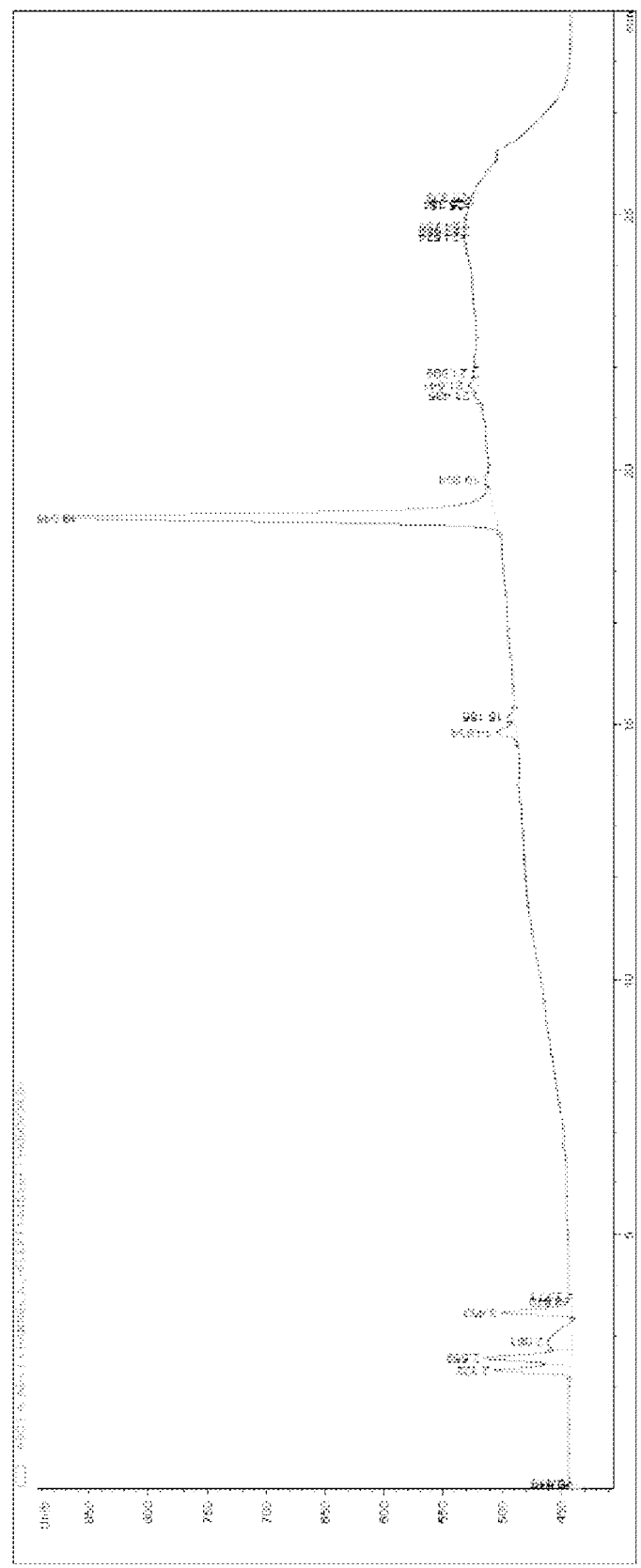
Figure 13C:
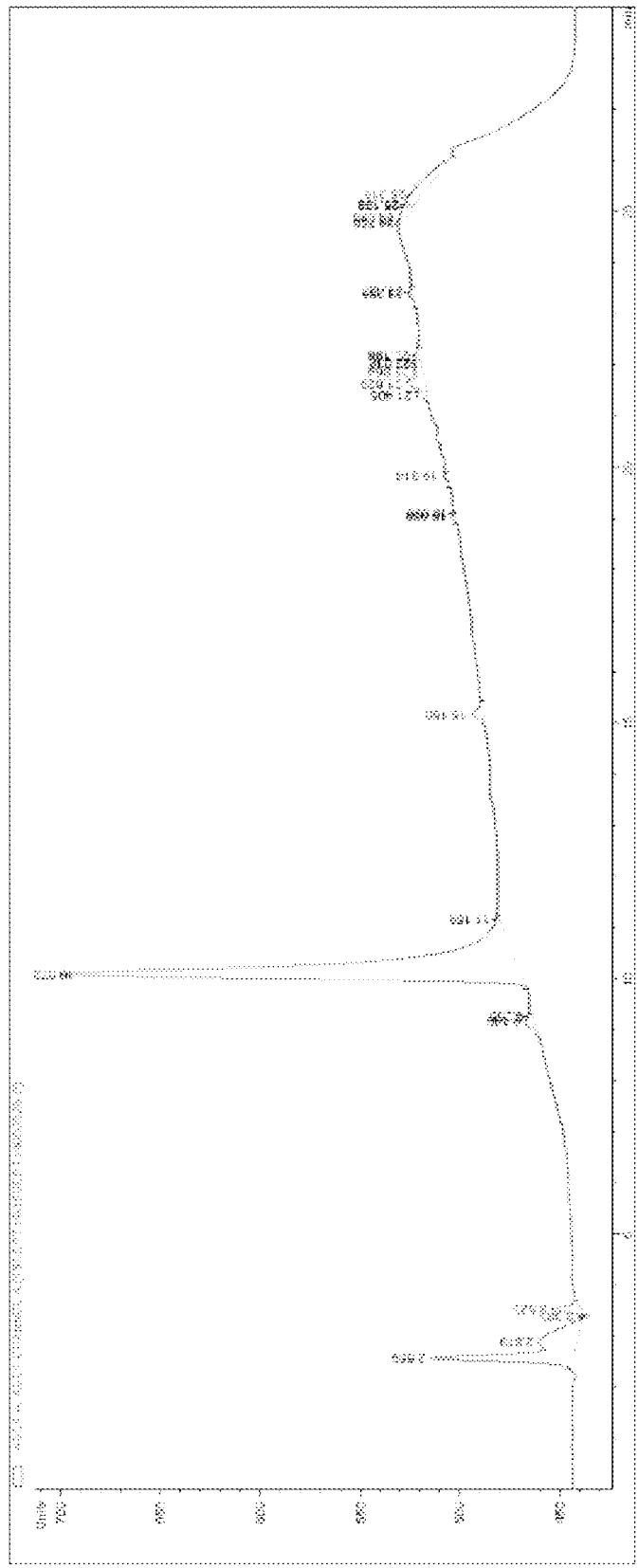
Figure 13D:
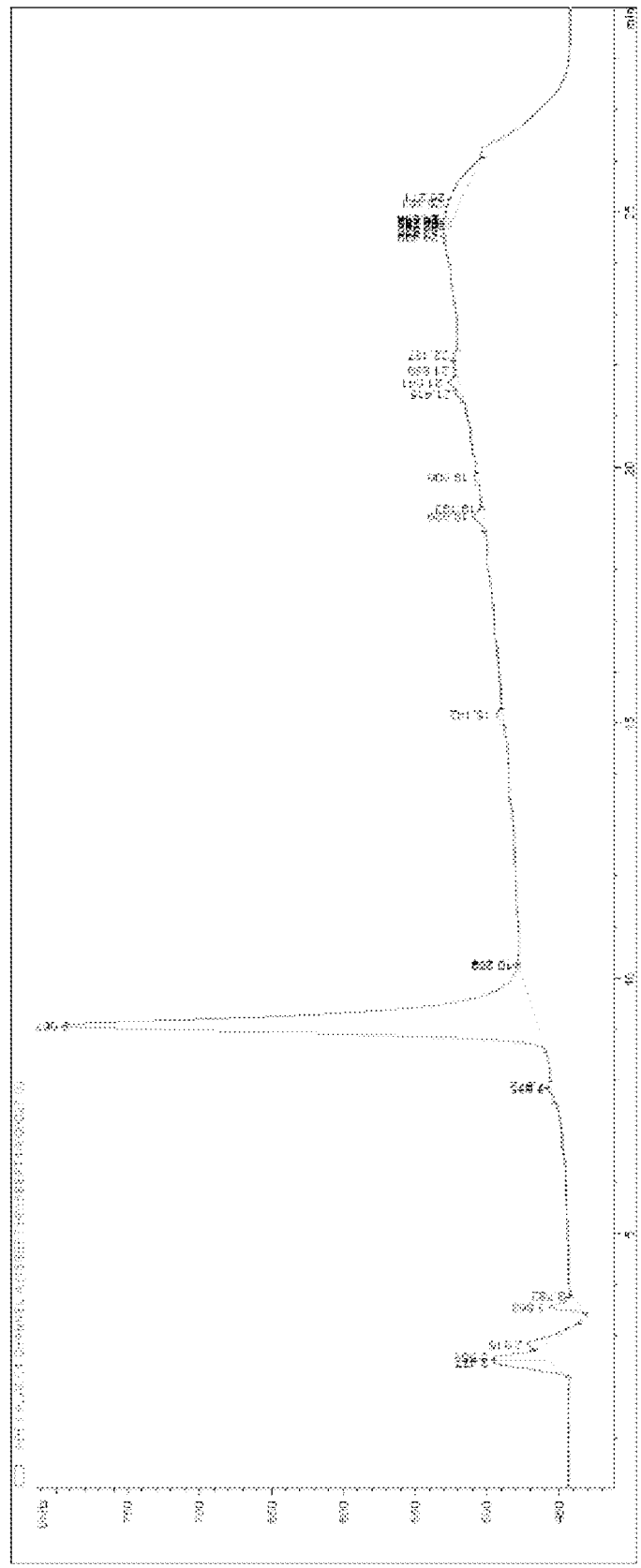

For untreated 6-fluoro-9-methyl-β-carboline (6F9MβC) a retention time of 19.0 minutes was measured (see FIG. 13A), while the reference measurements showed for 6-fluoro-2,9-dimethyl-β-carbolinium cation (6F29DMβC) a retention time of 10.1 minutes (see FIG. 130) and for 2,9-dimethyl-β-carbolinium cation (29DMβC) a retention time of 9.1 minutes (see FIG. 13D). All three reference samples also showed significantly from each other separably retention times. The 6-fluoro-9-methyl-β-carboline (100 µM) incubated with liver homogenates from the rat showed a peak at 19.0 minutes (also of 6F9MβC), but no peaks of 6-fluoro-2,9-dimethyl-β-carbolinium cation (6F29DMβC) or 2,9-dimethyl-β-carbolinium cation (29DMβC). Also, the tested lower concentrations of 6-fluoro-9-methyl-β-carboline (1 µM and 10 µm) showed identical results.

It can be concluded, that the inventive 6-fluoro-9-methyl-β-carboline under the given conditions fortunately does not metabolize to known toxic degradation products.

In the following, the synthesis of reference cations 6-fluoro-2,9-dimethyl-β-carbolinium cation (6F29DMβC) and 2,9-dimethyl-β-carbolinium cation (29DMβC) is described.

For the synthesis of 6F29DMβC, to a solution of 50 mg (i.e. 0.25 mmol) 6-fluoro-9-methyl-β-carboline (free base) in 3 mL acetonitrile is added 200 mg (i.e. 1.4 mmol) methyl iodide. The reaction mixture is stirred under nitrogen for 24 h at room temperature. Then solvents are removed by a stream of nitrogen. The yellow, fluorescent residue is recrystallyzed from a small amount of acetonitrile. Yield: 53 mg (i.e. 15 mmol) 60%.

For the synthesis of 29DMβC, to a solution of 50 mg (i.e. 0.27 mmol) 9-methyl-β-carboline (free base) in 3 mL acetonitrile is added 200 mg (i.e. 1.4 mmol) methyl iodide. The reaction mixture is stirred under nitrogen for 24 h at room temperature. Then solvents are removed by a stream of nitrogen. The yellow, fluorescent residue is recrystallyzed from a small amount of acetonitrile, filtered off and dried in vacuum. Yield: 43 mg (i.e. 13 mmol) 48%

Example 9

6-fluoro-9-methyl-β-carboline improves learning and memory

The underlying mechanisms of learning and memory are very complex. They can be considered on molecular and on cellular level, on the level of system biology and on the level of psychology. One of the key processes for memory formation on molecular level is the activation of the cAMP response element binding proteins (CREB). This leads to new formation of synapses, a process coupled to the memory formation. This process is regulated by many factors. A positive amplification is induced by the brain BDNF and its receptor TRKB. Therefore, the inventive 6-fluoro-9-methyl-β-carboline (6F9MβC) should be investigated on the cellular level.

We found out in our examinations on cellular level, that inventive 6-fluoro-9-methyl-β-carboline (6F9MβC) increases the concentration of CREB by a factor of 8 and increases the concentration of BDNF up to three times. These findings suggest, that 6F9MβC promotes learning and memory. This hypothesis was verified in the following experiment.

In an eight-armed labyrinth the effect of 6F9MβC on the learning behavior was tested. 5 months old male rats were got used to the experimenter in daily sessions for 10 days. Afterwards, they were allowed to explore the labyrinth in multiple sessions for 2 days and they also learnt that they get a food reward there. Then the food was reduced until the body weight was reduced by 10% of the starting weight. Afterwards, at each end of the 8 arms of the labyrinth food was placed and a camera installed that recorded every movement of the animal. On the first test day the rat was placed without a prior injection on the platform in the center of the labyrinth. At the next day 2 mg/kg body weight 6-fluoro-9-methyl-β-carboline (6F9MβC) as free base dissolved in physiological sodium chloride solution was administered intraperitoneally to the rat by the experimenter. 2 hours later the animal was placed on the platform in the center of the labyrinth from where it had access to all arms. This procedure was repeated daily until the animal only did one mistake, i.e. went in an arm, which it had already entered before in the corresponding session. At the end of the session all 8 arms had to be visited.

12 rats, that were treated with 6F9MβC and a control group of 12 rats, that only got physiological sodium chloride solution, were examined. The verum group (received 6F9MβC) reached the criteria after 6 days and the control group after 14 days. The difference was verified by ANOVA for repeated measurements and was significant (p<0.01). These results prove clearly, that 6F9MβC accelerates learning processes and improves memory. We could also verify our hypothesis.

This demonstrates, that the active agent 6F9MβC is not only effective against diseases of the inner ear, but also has beneficial influence on complex behavior like learning and memory.

REFERENCES

1.) Application of high-performance liquid chromatography based measurements of lipophilicity to model biological distribution. Valkó K *Journal of Chromatography A* 2004; 1037 (1-2): 299-310.
2.) The levels of norharman are high enough after smoking to affect monoamineoxidase B in platelets. Rommelspacher et al., Eu J Pharmacol 2002; 441 (1-2): 115-125.

The invention claimed is:

1. A compound of general formula (I):

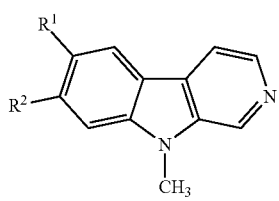

wherein:
R$^1$ is —F and R$^2$ is —H or —F, or
R$^1$ is —H and R$^2$ is —F; and
pharmacologically acceptable salts, solvates and hydrates of the aforementioned compounds.

2. The compound according to claim 1, wherein R$^1$ is —F and R$^2$ is —H.

3. A method for preparing a compound according to claim 1, comprising:
 a) reacting a starting material of general formula (II) under addition of glyoxylic acid hydrate of formula (III) and a base to form a compound of general formula (IV):

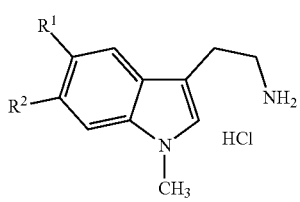

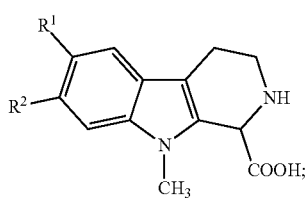

b) decarboxylating the compound of general formula (IV) under addition of an acid and under heating to form a compound of general formula (V):

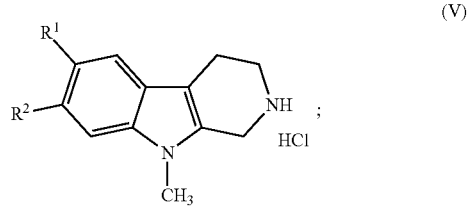

c) aromatizing the compound of general formula (V) to form a compound of general formula (I) under addition of a catalyst; and wherein:
R$^1$ is —F and R$^2$ is —H or —F, or
R$^1$ is —H and R$^2$ is —F.

4. The method according to claim 3, wherein in step c) the catalyst is Pd/C.

5. A method for treating a disease and/or damages of inner ear comprising administering an effective amount of a compound according to claim 1.

6. The method according to claim 5, wherein the diseases and/or damages of the inner ear is an acute diseases of the inner ear selected from the group consisting of blast trauma, blast injury of the ear, hearing loss, and insertion trauma.

7. The method according to claim 5, wherein the diseases and/or damages of the inner ear is a chronic disease of the inner ear selected from the group consisting of chronic acoustic trauma, tinnitus, and presbyacusis.

8. The method according to claim 5, wherein the damage of the inner ear is caused by ototoxic substances.

9. A pharmaceutical composition comprising at least one compound according to claim 1.

10. The pharmaceutical composition of claim 9, wherein the pharmaceutical composition is in a form of droplet, ointment, spray, liposome, gel, emulsion, or injection solution.

* * * * *

UNITED STATES PATENT AND TRADEMARK OFFICE
CERTIFICATE OF CORRECTION

PATENT NO.        : 9,630,964 B2
APPLICATION NO.   : 15/025538
DATED             : April 25, 2017
INVENTOR(S)       : Hans Rommelspacher Page 1 of 4

It is certified that error appears in the above-identified patent and that said Letters Patent is hereby corrected as shown below:

In Column 5 at Line 17 (approx.), Change "(glyconic" to --(glycolic--.

In Column 5 at Line 27 (approx.), Change "camphersulfonic" to --camphorsulfonic--.

In Column 5 at Line 33 (approx.), After "possible" insert --.--.

In Column 7 at Line 19 (approx.), Change "formular" to --formula--.

In Column 8 at Line 9 (approx.), Change "camphersulfonic" to --camphorsulfonic--.

In Column 8 at Line 10 (approx.), Change "hydrogenebenzenesulfonic" to --hydrogenbenzenesulfonic--.

In Column 8 at Line 18 (approx.), After "(I)" insert --:--.

In Column 8 at Lines 41-44, Delete "The compound 6-fluoro-9-methyl-β-carboline will be herein partly also abbreviated to "6F9MβC" or "AC102". The 9-methyl-β-carboline known in the prior art will be on the other hand partly abbreviated to "9MβC" or "AC002." and insert the same on Column 8, Line 40, as a continuation of the same paragraph.

In Column 8 at Line 44, Change ""AC002." to --"AC002".--.

In Column 9 at Line 19 (approx.), After "(Ia)" insert --:--.

In Column 9 at Line 44, Change "(glyconic" to --(glycolic--.

In Column 9 at Line 46, Change "acide)," to --acid),--.

Signed and Sealed this
Third Day of October, 2017

Joseph Matal
*Performing the Functions and Duties of the
Under Secretary of Commerce for Intellectual Property and
Director of the United States Patent and Trademark Office*

In Column 9 at Line 54, Change "camphersulfonic" to --camphorsulfonic--.

In Column 9 at Line 60, After "possible" insert --.--.

In Column 11 at Line 19, Change "camphersulfonic" to --camphorsulfonic--.

In Column 11 at Line 20, Change "hydrogenebenzenesulfonic" to --hydrogenbenzenesulfonic--.

In Column 11 at Line 38, Change "compound compound" to --compound--.

In Column 12 at Line 11, After "(Ib)" insert --:--.

In Column 12 at Lines 44-45, Change "camphersulfonic" to --camphorsulfonic--.

In Column 12 at Line 50, After "possible" insert --.--.

In Column 13 at Line 33, Change "Kanada)." to --Canada).--.

In Column 14 at Line 10, Change "camphersulfonic" to --camphorsulfonic--.

In Column 14 at Line 11, Change "hydrogenebenzenesulfonic" to --hydrogenbenzenesulfonic--.

In Column 15 at Line 40, Change "ceftmetazol," to --cefmetazole,--.

In Column 15 at Line 40, Change "ioracarbef," to --loracarbef,--.

In Column 15 at Line 45, Change "ansymacin, oelandomycin," to --ansamycin, oleandomycin,--.

In Column 15 at Line 59, Change "quinopristin," to --quinupristin,--.

In Column 15 at Line 60, Change "isoniazide," to --isoniazid,--.

In Column 16 at Lines 2-3, Change "itroconazole," to --itraconazole,--.

In Column 18 at Line 10 (approx.), After "solvent" insert --.--.

In Column 18 at Line 37, After "compositions" insert --.--.

In Column 19 at Line 48, Change "polyoxameres," to --poloxamers,--.

In Column 20 at Line 67, After "likewise" insert --.--.

In Column 22 at Line 24 (approx.), Change "dichlorofuoromethane," to --dichlorofluoromethane,--.

In Column 22 at Line 62, Change "gloxylic" to --glyoxylic--.

CERTIFICATE OF CORRECTION (continued)
U.S. Pat. No. 9,630,964 B2

In Column 23 at Lines 5-6, Change "gloxylic" to --glyoxylic--.

In Column 23 at Lines 10-11, Change "gloxylic" to --glyoxylic--.

In Column 23 at Line 15, After "carboline)" insert --.--.

In Column 23 at Line 17, After "carboline)" insert --.--.

In Column 23 at Line 36, After "[45/55]" insert --.--.

In Column 23 at Line 47, Change "(10 µM." to --(10 µM,--.

In Column 24 at Line 54, After "[45/55]" insert --.--.

In Column 25 at Line 2, After "[45/55]" insert --.--.

In Column 25 at Line 33, Change "melting" to --Melting--.

In Column 25 at Line 44, Change "C," to --C:--.

In Column 25 at Line 44, Change "H," to --H:--.

In Column 25 at Line 44, Change "N," to --N:--.

In Column 25 at Line 44, Change "C," to --C:--.

In Column 25 at Line 45, Change "H," to --H:--.

In Column 25 at Line 45, Change "N," to --N:--.

In Column 25 at Line 57, Change "hydroxyide" to --hydroxide--.

In Column 27 at Lines 1-17, Delete "Experimentally, the lipophilicity is determined by either actual distribution between octanol and water or more easily, as described by Valkó, by HPLC experiments with reversed-phase columns (RP18) (K. Valkó; Journal of Chromatography A 2004, 1037 (1-2), 299-310). Herein the components of the substance to investigate interact differently strong with the stationary phase. If the interaction of a component with the stationary phase is weaker, then it exits the column earlier. Depending on the strength of these interactions the components of the substance appear at different times (at retention times) at the end of the separation column. Such experiments were conducted with both substances. It was shown, that the inventive compound 6-fluoro-9-methyl-β-carboline has a longer retention time than 9-methyl-β-carboline (FIG. 4), which indicates clearly a higher lipophilicity of 6-fluoro-9-methyl-β-carboline regarding the selected column as well as stationary phase." and insert the same on Column 26, Line 67, as a continuation of the same paragraph.

In Column 28 at Line 39, Change "neurotophic" to --neurotrophic--.

In Column 32 at Line 41, Change "cellurar" to --cellular--.

In Column 33 at Line 49, Change "Bepanten" to --Bepanthen--.

In Column 34 at Line 22 (approx.), Change "serumalbumine" to --serum albumin--.

In Column 34 at Line 57, Change "Bepanten" to --Bepanthen--.

In Column 35 at Line 7, Change "(hierin" to --(herein--.

In Column 37 at Lines 1-2, Change "recrystallyzed" to --recrystallized--.

In Column 37 at Line 9, Change "recrystallyzed" to --recrystallized--.

In Column 37 at Line 11, After "48%" insert --.--.

In Column 45 at Lines 14-21 (approx.), In Claim 1, change " 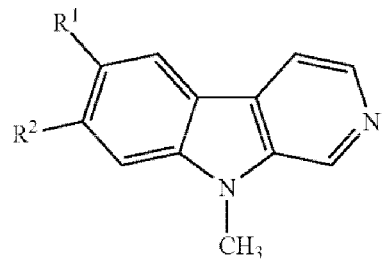 " to -- 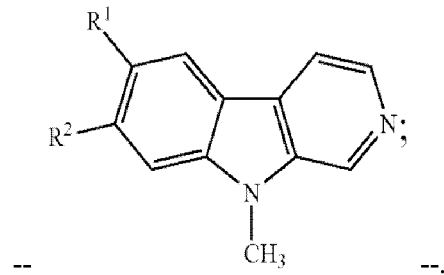 --.

In Column 46 at Line 39 (approx.), In Claim 6, change "diseases" to --disease--.

In Column 46 at Line 40 (approx.), In Claim 6, change "damages" to --damage--.

In Column 46 at Line 43, In Claim 7, change "diseases" to --disease--.

In Column 46 at Line 44, In Claim 7, change "damages" to --damage--.

SEQUENCE LISTING

<160> NUMBER OF SEQ ID NOS: 22

<210> SEQ ID NO 1
<211> LENGTH: 18
<212> TYPE: DNA
<213> ORGANISM: Artificial Sequence
<220> FEATURE:
<223> OTHER INFORMATION: Forward Primer f?r BDNF

<400> SEQUENCE: 1
ggatgaggac cagaaagt                                                 18

<210> SEQ ID NO 2
<211> LENGTH: 19
<212> TYPE: DNA
<213> ORGANISM: Artificial Sequence
<220> FEATURE:
<223> OTHER INFORMATION: Reverse Primer f?r BDNF

<400> SEQUENCE: 2
agcagaaaga gaagaggag                                                19

<210> SEQ ID NO 3

```
<211> LENGTH: 22
<212> TYPE: DNA
<213> ORGANISM: Artificial Sequence
<220> FEATURE:
<223> OTHER INFORMATION: Forward Primer f?r Lif

<400> SEQUENCE: 3
ccaacaacct ggacaagcta tg                                              22

<210> SEQ ID NO 4
<211> LENGTH: 20
<212> TYPE: DNA
<213> ORGANISM: Artificial Sequence
<220> FEATURE:
<223> OTHER INFORMATION: Reverse Primer f?r Lif

<400> SEQUENCE: 4
gtggcgttga gcttgctgtg                                                 20

<210> SEQ ID NO 5
<211> LENGTH: 18
<212> TYPE: DNA
<213> ORGANISM: Artificial Sequence
<220> FEATURE:
<223> OTHER INFORMATION: Forward Primer f?r NT3

<400> SEQUENCE: 5
cggagcataa gagtcacc                                                   18

<210> SEQ ID NO 6
<211> LENGTH: 18
<212> TYPE: DNA
<213> ORGANISM: Artificial Sequence
<220> FEATURE:
<223> OTHER INFORMATION: Reverse Primer f?r NT3

<400> SEQUENCE: 6
cctggcttcc ttacatcg                                                   18

<210> SEQ ID NO 7
<211> LENGTH: 20
<212> TYPE: DNA
<213> ORGANISM: Artificial Sequence
<220> FEATURE:
<223> OTHER INFORMATION: Forward Primer f?r Id2

<400> SEQUENCE: 7
catcctgtcc ttgcaggctt                                                 20

<210> SEQ ID NO 8
<211> LENGTH: 23
<212> TYPE: DNA
<213> ORGANISM: Artificial Sequence
<220> FEATURE:
<223> OTHER INFORMATION: Reverse Primer f?r Id2

<400> SEQUENCE: 8
ccattcaact tgtcctcctt gtg                                             23

<210> SEQ ID NO 9
<211> LENGTH: 20
<212> TYPE: DNA
<213> ORGANISM: Artificial Sequence
<220> FEATURE:
<223> OTHER INFORMATION: Forward Primer f?r BTG2

<400> SEQUENCE: 9
```
caggaggcac tcacagagca                                                    20

<210> SEQ ID NO 10
<211> LENGTH: 21
<212> TYPE: DNA
<213> ORGANISM: Artificial Sequence
<220> FEATURE:
<223> OTHER INFORMATION: Reverse Primer f?r BTG2

<400> SEQUENCE: 10
aatgcggtag gacacctcat a                                                  21

<210> SEQ ID NO 11
<211> LENGTH: 17
<212> TYPE: DNA
<213> ORGANISM: Artificial Sequence
<220> FEATURE:
<223> OTHER INFORMATION: Forward Primer f?r Cbln

<400> SEQUENCE: 11
caagtgcctg gtggtgt                                                       17

<210> SEQ ID NO 12
<211> LENGTH: 25
<212> TYPE: DNA
<213> ORGANISM: Artificial Sequence
<220> FEATURE:
<223> OTHER INFORMATION: Reverse Primer f?r Cbln

<400> SEQUENCE: 12
gttcactagt acctggtcga agtag                                              25

<210> SEQ ID NO 13
<211> LENGTH: 23
<212> TYPE: DNA
<213> ORGANISM: Artificial Sequence
<220> FEATURE:
<223> OTHER INFORMATION: Forward Primer f?r DRD2S

<400> SEQUENCE: 13
ggactcaata acgcagacca gaa                                                23

<210> SEQ ID NO 14
<211> LENGTH: 18
<212> TYPE: DNA
<213> ORGANISM: Artificial Sequence
<220> FEATURE:
<223> OTHER INFORMATION: Reverse Primer f?r DRD2S

<400> SEQUENCE: 14
cgggcagcct cctttagt                                                      18

<210> SEQ ID NO 15
<211> LENGTH: 20
<212> TYPE: DNA
<213> ORGANISM: Artificial Sequence
<220> FEATURE:
<223> OTHER INFORMATION: Forward Primer f?r DKK1

<400> SEQUENCE: 15
cattgacaac taccagccgt                                                    20

<210> SEQ ID NO 16
<211> LENGTH: 24
<212> TYPE: DNA

<213> ORGANISM: Artificial Sequence
<220> FEATURE:
<223> OTHER INFORMATION: Reverse Primer f?r DKK1

<400> SEQUENCE: 16
atcagaagac acacatattc catt                                              24

<210> SEQ ID NO 17
<211> LENGTH: 20
<212> TYPE: DNA
<213> ORGANISM: Artificial Sequence
<220> FEATURE:
<223> OTHER INFORMATION: Forward Primer f?r Bax

<400> SEQUENCE: 17
gatgattgcc gccgtggaca                                                   20

<210> SEQ ID NO 18
<211> LENGTH: 21
<212> TYPE: DNA
<213> ORGANISM: Artificial Sequence
<220> FEATURE:
<223> OTHER INFORMATION: Reverse Primer f?r Bax

<400> SEQUENCE: 18
caccttggtg cacagggcct t                                                 21

<210> SEQ ID NO 19
<211> LENGTH: 18
<212> TYPE: DNA
<213> ORGANISM: Artificial Sequence
<220> FEATURE:
<223> OTHER INFORMATION: Forward Primer f?r Bcl2

<400> SEQUENCE: 19
gtgtggagag cgtcaacc                                                     18

<210> SEQ ID NO 20
<211> LENGTH: 19
<212> TYPE: DNA
<213> ORGANISM: Artificial Sequence
<220> FEATURE:
<223> OTHER INFORMATION: Reverse Primer f?r Bcl2

<400> SEQUENCE: 20
cttcagagac agccaggag                                                    19

<210> SEQ ID NO 21
<211> LENGTH: 24
<212> TYPE: DNA
<213> ORGANISM: Artificial Sequence
<220> FEATURE:
<223> OTHER INFORMATION: Forward Primer f?r B2M (Referenzgen)

<400> SEQUENCE: 21
actggtcttt ctatctcttg tact                                              24

<210> SEQ ID NO 22
<211> LENGTH: 20
<212> TYPE: DNA
<213> ORGANISM: Artificial Sequence

```
<220> FEATURE:
<223> OTHER INFORMATION: Reverse Primer f?r B2M (Referenzgen)

<400> SEQUENCE: 22
cttcaaacct ccatgatgct                                          20
```